(12) United States Patent
Tanaka et al.

(10) Patent No.: US 9,307,950 B2
(45) Date of Patent: Apr. 12, 2016

(54) SLEEP APNEA SYNDROME TESTING APPARATUS, TEST METHOD FOR SLEEP APNEA SYNDROME AND TANGIBLE RECORDING MEDIUM RECORDING PROGRAM

(75) Inventors: Masakiyo Tanaka, Kawasaki (JP); Masanao Suzuki, Kawasaki (JP); Yasuji Ota, Kawasaki (JP)

(73) Assignee: FUJITSU LIMITED, Kawasaki (JP)

( * ) Notice: Subject to any disclaimer, the term of this patent is extended or adjusted under 35 U.S.C. 154(b) by 670 days.

(21) Appl. No.: 13/355,860

(22) Filed: Jan. 23, 2012

(65) Prior Publication Data

US 2012/0190996 A1    Jul. 26, 2012

Related U.S. Application Data

(63) Continuation of application No. PCT/JP2009/063255, filed on Jul. 24, 2009.

(51) Int. Cl.
| | |
|---|---|
| *A61B 5/08* | (2006.01) |
| *A61B 7/00* | (2006.01) |
| *A61B 5/00* | (2006.01) |

(52) U.S. Cl.
CPC .............. *A61B 7/003* (2013.01); *A61B 5/4818* (2013.01); *A61B 5/7257* (2013.01)

(58) Field of Classification Search
CPC .... A61B 5/0823; A61B 5/0826; A61B 5/087; A61B 7/003
USPC .......................................... 600/529–543, 586
See application file for complete search history.

(56) References Cited

U.S. PATENT DOCUMENTS

| 5,522,382 A | 6/1996 | Sullivan et al. |
| 6,168,568 B1 * | 1/2001 | Gavriely ........................ 600/529 |
| 6,290,654 B1 * | 9/2001 | Karakasoglu .................. 600/529 |

(Continued)

FOREIGN PATENT DOCUMENTS

| JP | 2001-29328 | 2/2001 |
| JP | 2003-339674 | 12/2003 |

(Continued)

OTHER PUBLICATIONS

Nakano Hiroshi, "Measurement of Snoring in Sleep Apnea Syndrome." The Japanese Journal of Chest Diseases, vol. 63 No. 7, Jul. 2004 pp. 644-653.*
European Search Report dated Jun. 11, 2013, from corresponding European Application No. 09847569.2-1660.

(Continued)

*Primary Examiner* — Navin Natnithithadha
*Assistant Examiner* — Meredith Weare
(74) *Attorney, Agent, or Firm* — Katten Muchin Rosenman LLP

(57) ABSTRACT

A sleep apnea syndrome testing apparatus includes: an analyzing unit that analyzes every unit time a sound signal resulting from a subject during sleep; a determining unit that determines whether a unit time of the sound signal includes a breath sound or a characteristic sound produced when a patient with sleep apnea syndrome recovers from an apneic state into a breathing state, and the determining unit that determines that the sleep state of the subject in the unit time is any one of "breathing restored state," "state with breathing," and "state without breathing;" a storage unit in which a sleep state of the subject in each unit time is stored; and a detecting unit that detects an apneic state of the subject if a history of the sleep states of the subject indicates at least a transition from the "state without breathing" to the "breathing restored state."

9 Claims, 21 Drawing Sheets

(56) References Cited

U.S. PATENT DOCUMENTS

| | | | |
|---|---|---|---|
| 7,153,278 B2* | 12/2006 | Ono | A61B 7/003 600/324 |
| 7,567,900 B2* | 7/2009 | Suzuki et al. | 704/233 |
| 2004/0010202 A1 | 1/2004 | Nakatani et al. | |
| 2005/0043645 A1* | 2/2005 | Ono | A61B 7/003 600/529 |
| 2005/0113711 A1 | 5/2005 | Nakatani et al. | |
| 2006/0053003 A1* | 3/2006 | Suzuki et al. | 704/216 |
| 2007/0010722 A1 | 1/2007 | Suzuki et al. | |
| 2008/0243014 A1* | 10/2008 | Moussavi et al. | 600/529 |
| 2008/0319333 A1* | 12/2008 | Gavish et al. | 600/529 |

FOREIGN PATENT DOCUMENTS

| | | |
|---|---|---|
| JP | 2004-24684 | 1/2004 |
| JP | 2005-152328 | 6/2005 |
| JP | 2005-304941 | 11/2005 |
| JP | 2007-14501 | 1/2007 |
| JP | 2007-61203 | 3/2007 |
| JP | 2007-300951 | 11/2007 |
| WO | 02/13697 | 2/2002 |

OTHER PUBLICATIONS

Hiroshi Nakano. "Measurement of Snoring in Sleep Apnea Syndrome" The Japanese Journal of Chest Diseases, vol. 63, No. 7, Jul. 2004, pp. 644-653.

* cited by examiner

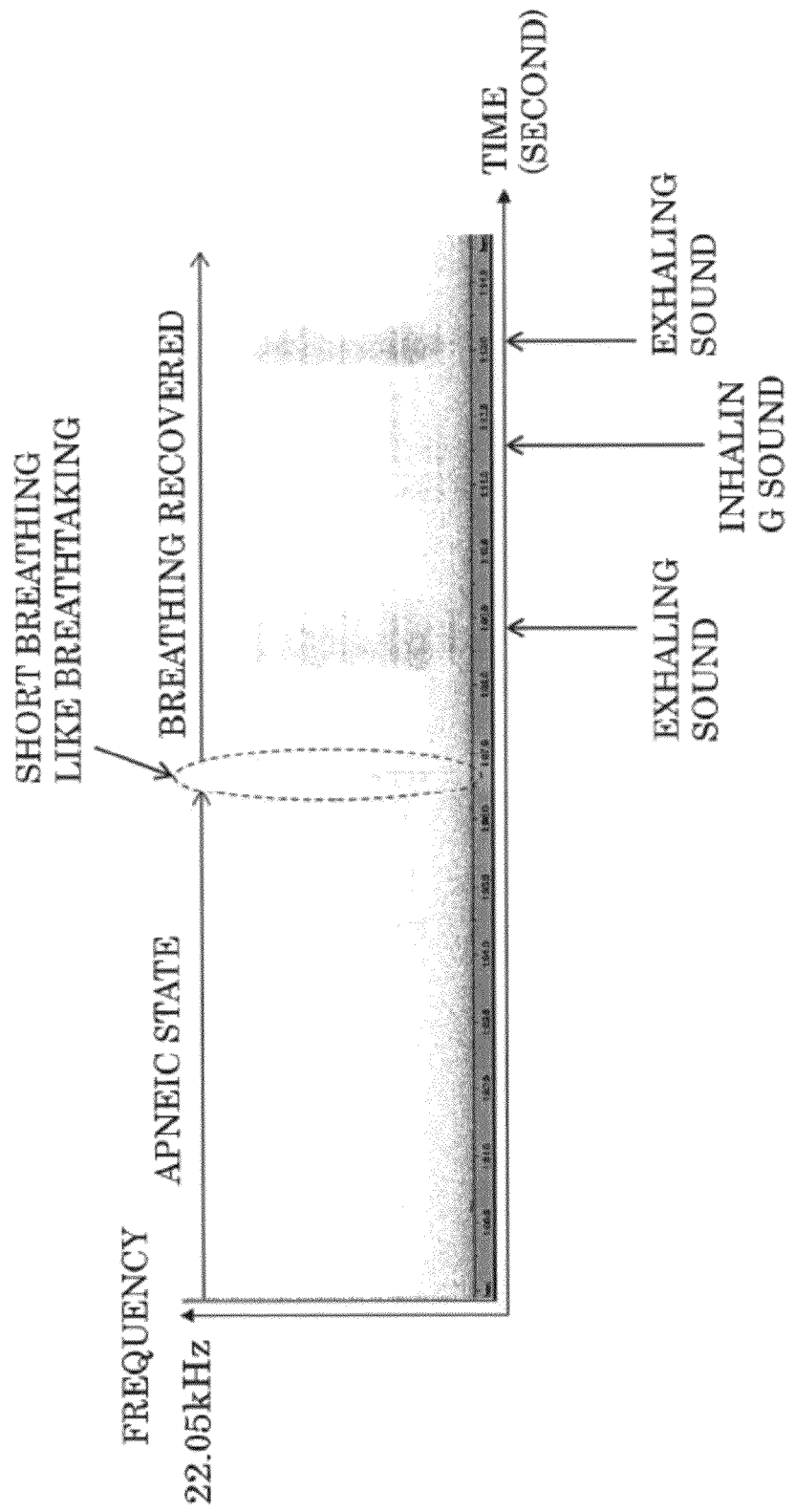

FIG. 6

| STATE | DURATION | THE NUMBER OF FORMANTS | VARIANCE OF FINE STRUCTURE POWER SPECTRUM |
|---|---|---|---|
| BREATH SOUND | 0.5~2.0 SECOND | 0~1 | MEDIUM |
| CHARACTERISTIC SOUND A (SHORT BREATHING) | 0.2~0.3 SECOND | 0~1 | MEDIUM |
| CHARACTERISTIC SOUND B (GROAN) | 0.1~0.3 SECOND | 2~4 | GREAT |
| CHARACTERISTIC SOUND C (RUSTLING SOUND OF BEDCLOTHES) | 0.5~3.0 SECOND | 0 | SMALL |

SLEEP APNEA SYNDROME TESTING APPARATUS, TEST METHOD FOR SLEEP APNEA SYNDROME AND TANGIBLE RECORDING MEDIUM RECORDING PROGRAM

CROSS-REFERENCE TO RELATED APPLICATION

This is a continuation of Application PCT/JP2009/063255, filed on Jul. 24, 2009, now pending, the entire contents of which are incorporated herein by reference.

FIELD

The present invention relates to a sleep apnea syndrome testing apparatus for detecting an apneic state during sleep.

BACKGROUND

Sleep apnea syndrome is defined as a condition in which an apneic state where breathing stops for ten seconds or longer is repeated 30 times or more during seven hours of sleep or is repeated five times or more per hour of sleep. Sleep apnea syndrome causes symptoms such as uncontrollable daytime sleepiness, depression, impaired concentration, and snoring. Further, since a patient developing sleep apnea syndrome is sleeping, if the patient does not live with anyone such as his/her family in the same house, discovery of sleep apnea syndrome is often delayed.

For a close examination of sleep apnea syndrome, a patient needs to enter a hospital having a room in which an apparatus for acquiring data used in the examination is installed, and a medical specialist needs to analyze the data. That is, a patient has a burden of costs and time and also has a physical burden since the patient often needs to be equipped with a sensor. Further, in such a close examination of sleep apnea syndrome, the number of patients who can be examined at a time is limited, which is inefficient for hospitals.

In view of such circumstances, there is a need for a simple test method that can test at home or the like beforehand whether or not a close examination of sleep apnea syndrome is needed.

PATENT DOCUMENT

[Patent document 1] Japanese Laid-open Patent Publication No. 2001-29328

SUMMARY

According to one aspect of the invention, a sleep apnea syndrome testing apparatus including:

an analyzing unit that analyzes a sound signal resulting from a subject during sleep and collected by a sound pickup device; and a determining unit that determines, based on an analysis result by the analyzing unit, whether or not the sound signal includes a characteristic sound produced when a sleep state of the subject recovers from an apneic state into a breathing state.

Another aspect of the present invention is such a test method for sleep apnea syndrome as described above. Further aspects of the present invention may include a program for causing an information processing apparatus to function as a sleep apnea syndrome testing apparatus, and a computer readable recording medium on which the program is recorded.

The object and advantage of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1A is a graph depicting examples of frequency spectrums of sound signals including the characteristic sound;

FIG. 6 is an example of a table in which the frequency characteristics of the breath sound, the characteristic sound A, the characteristic sound B, and the characteristic sound C are organized;

DESCRIPTION OF EMBODIMENTS

Embodiments for carrying out the present invention (hereinafter, referred to as the embodiments) will now be described with reference to the drawings. Configurations of the following embodiments are illustrative, and the present invention is not limited thereto.

First Embodiment

A sleep apnea syndrome testing apparatus in a first embodiment will be described. A microphone is installed as a sound pickup device at an appropriate position close to a sleeping place of a subject, and sound signals from the subject and around the subject are collected. That is, the subject is examined in a usual sleeping state without restrictions such as being equipped with a sensor. The sleep apnea syndrome testing apparatus in the first embodiment analyzes the sound signals resulting from the sleeping subject and collected by the microphone, and determines frequency characteristics, thereby detecting an apneic state of the subject during sleep.

A study conducted by the present inventors on sound signals during sleep indicate that immediately before or after a subject in an apneic state recovers from the apneic state, that is, immediately before or after the transition from the apneic state to a breathing state, characteristic sounds occur as described later. Hereinafter, characteristic sounds produced by a patient in an apneic state immediately before or after the transition from an apneic state to a breathing state are referred to as the "characteristic sounds." The sleep apnea syndrome testing apparatus in the first embodiment detects an apneic state during sleep by using characteristic sounds that tend to be produced when a patient of sleep apnea syndrome recovers from an apneic state.

The characteristic sounds found by the study include the following.

(Characteristic sound A): an about 0.2 to 0.3-second short breath sound like a sound heard when a person takes breath or is surprised.

(Characteristic sound B): a short groan.

(Characteristic sound C): a sound resulting from the movement of a patient's body. For example, a sound of friction between a patient and bedclothes, produced by the patient moving his/her body.

All of the characteristic sounds are supposedly produced when a patient in an apneic state suffers the lack of oxygen in the body.

Figure 1B:
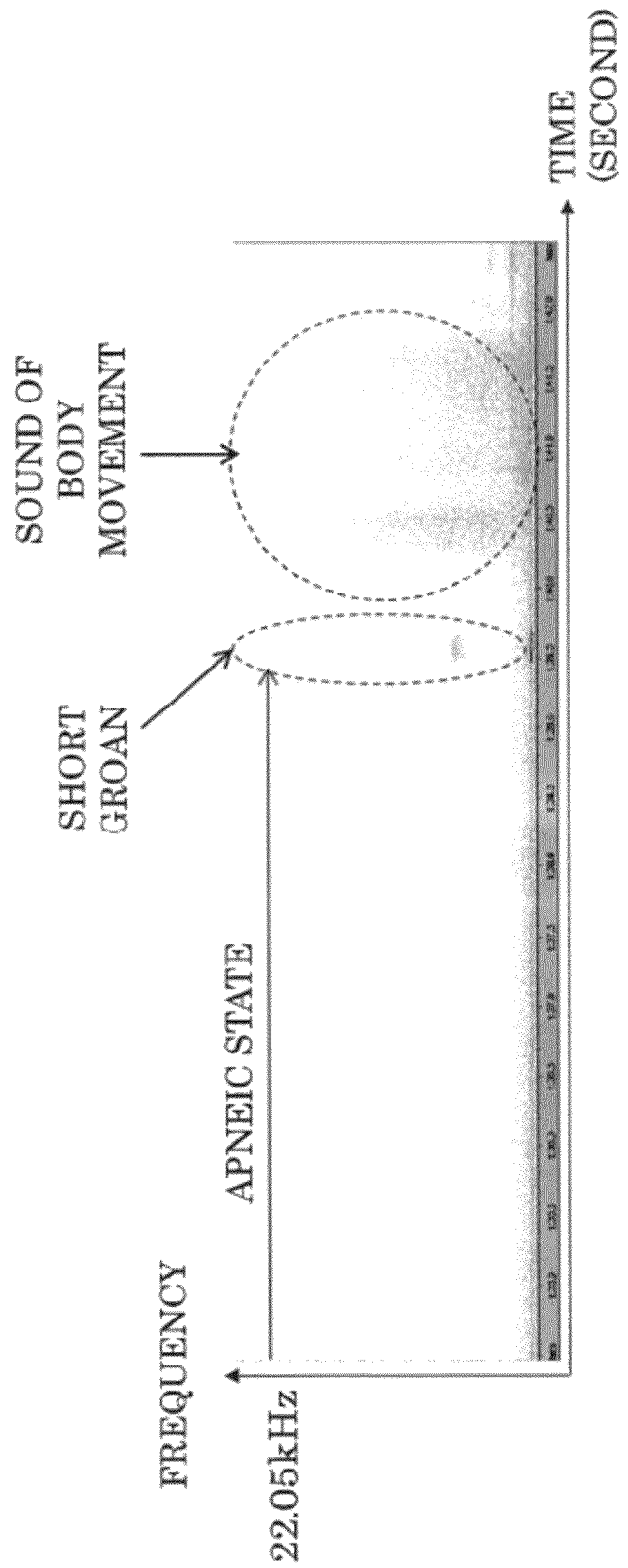
FIG. 1B is a graph depicting examples of frequency spectrums of sound signals including the characteristic sound.

FIG. 1A and FIG. 1B are graphs depicting examples of frequency spectrums of sound signals including the characteristic sound A, the characteristic sound B, and the characteristic sound C. In each of the graphs illustrated in FIG. 1A and FIG. 1B, a horizontal axis represents time, a vertical axis represents a frequency, and gradations represent the magnitude of frequency components.

In FIG. 1A, a part surrounded by a dotted line represents a characteristic sound A (a short breath sound like a sound of patient's breathtaking). Until the characteristic sound A, the breathing of the patient remains stopped, that is, the patient is in an apneic state, while after the characteristic sound A, exhaling and inhaling sounds of the patient are repeated. This indicates that the breathing has been restored after the characteristic sound A.

In FIG. 1B, a first part surrounded by a dotted line represents a characteristic sound B (a short groan). A second part surrounded by a dotted line represents a characteristic sound C (a sound of body movement or a rustling sound of bedclothes produced by body movement). Until the characteristic sound B, it is indicated that the breathing of the patient remains stopped, that is, the patient is in an apneic state. Further, although not illustrated in FIG. 1B, after the characteristic sound C, similarly to FIG. 1A, exhaling and inhaling sounds of the patient are repeated, so that the breathing has been restored.

The characteristic sound A, the characteristic sound B, and the characteristic sound C may be separately produced, or as illustrated in FIG. 1B, two or more of these sounds may be produced in combination.

<<A Configuration Example of the Sleep Apnea Syndrome Testing Apparatus>>

Figure 2:
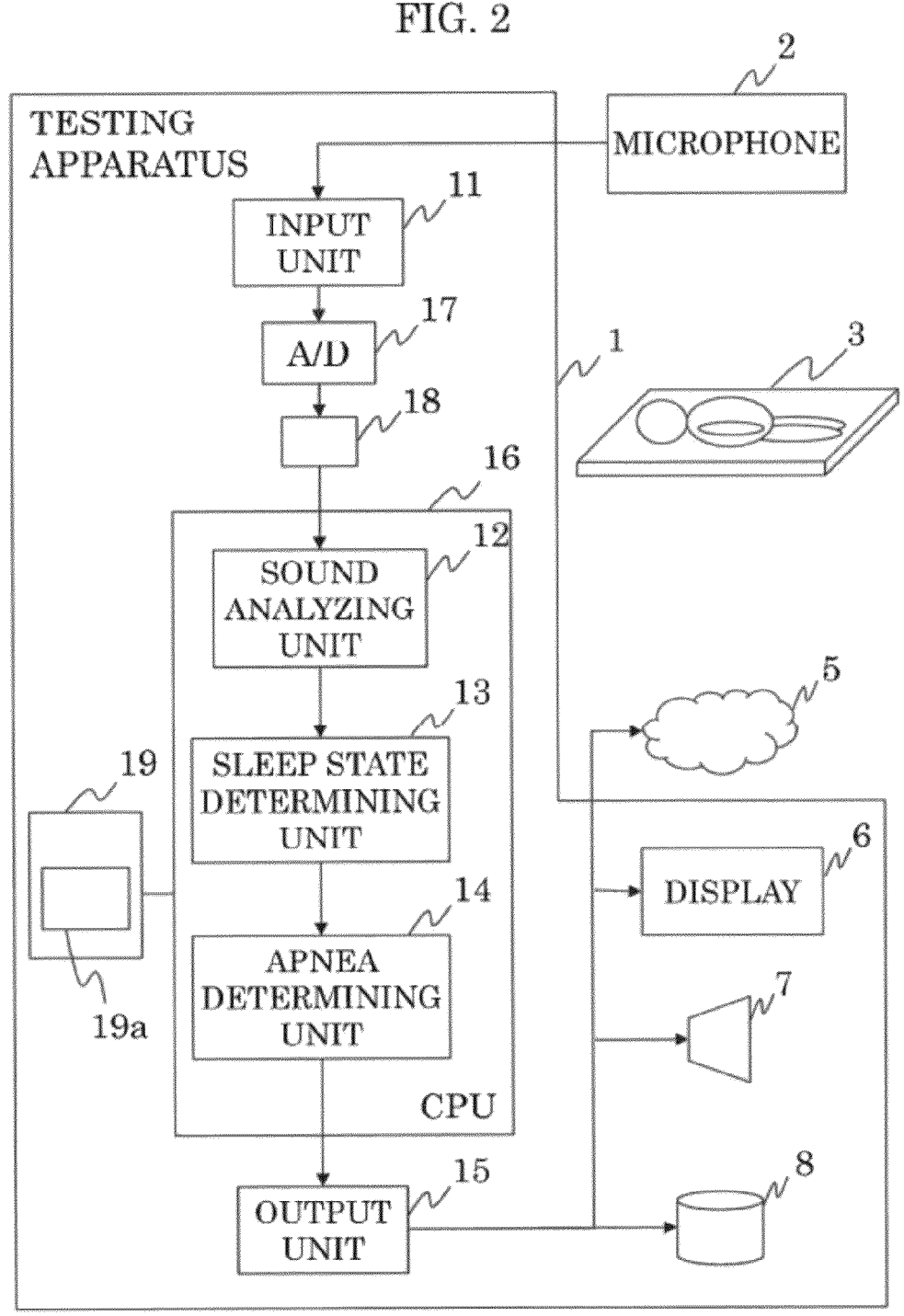
FIG. 2 is a diagram depicting a configuration example of a sleep apnea syndrome testing system.

FIG. 2 is a diagram depicting a configuration example of a sleep apnea syndrome testing system. The sleep apnea syndrome testing system includes a sleep apnea syndrome testing apparatus 1 (hereinafter, simply referred to as the testing apparatus 1), and a microphone 2 that collects sounds produced by a subject 3.

The testing apparatus 1 is an apparatus that detects an apneic state of the subject 3 by using a characteristic sound A, a characteristic sound B, and a characteristic sound C as depicted in FIG. 1A and FIG. 1B.

The microphone 2 is installed at a position close to the subject 3 where the microphone 2 can accurately collect a voice from the subject 3 and a body movement sound of the subject 3, and the microphone 2 faces the subject 3. The microphone 2 is installed, for example, above a sleeping place of the subject 3.

The microphone 2 is connected with the testing apparatus 1. The microphone 2 collects signals of breath sounds and voices from the subject 3 and sounds around the subject including body movement sounds of the subject 3. The microphone 2 outputs electrical signals of the collected sounds to the testing apparatus 1. Hereinafter, the electrical signals of the sounds are referred to as the "sound signals."

The testing apparatus 1 is connected with the microphone 2, and obtains the sound signal from the microphone 2 as input. The testing apparatus 1 analyzes the input sound signal and detects an apneic state of the subject based on an analysis result. The testing apparatus 1 outputs a detection result of the apneic state to at least one of a network 5, a display 6, a speaker 7, and secondary storage 8 which are connected with the testing apparatus 1.

The testing apparatus 1 includes an input unit 11, an output unit 15, a CPU (Central Processing Unit) 16, an analog-digital converter (A/D converter) 17, a buffer 18, and main memory 19. As a testing apparatus, an information processing apparatus may be adopted.

The input unit 11 is an interface to an external inputting device. The input unit 11 receives sound signals from the microphone 2. The input unit 11 outputs the received sound signals to the A/D converter 17.

The A/D converter 17 obtains the sound signals as input. The A/D converter 17 converts the sound signals from analog signals into digital signals. The A/D converter 17 outputs sound data converted into the digital signals to the buffer 18.

The buffer 18 obtains from the A/D converter 17 the sound data converted into the digital signals as input. The buffer 18 buffers the input sound data.

The CPU 16 sequentially extracts one frame of the sound signals from the buffer 18 and performs processing. The one frame is a unit time length. The one frame is defined as, for example, one to a few seconds. Hereinafter, the one frame of the sound signal is referred to as the sound frame.

The main memory 19 holds a sleep apnea syndrome testing program 19a loaded into a working space. The CPU 16 acts as a sound analyzing unit 12, a sleep state determining unit 13, and an apnea determining unit 14 by reading out the sleep apnea syndrome testing program 19a from the main memory 19 and executing the testing program 19a.

The sound analyzing unit 12 obtains a sound frame as input. The sound analyzing unit 12 analyzes the sound frame to calculate a feature amount of the sound frame. Examples of the feature amounts include a frequency spectrum of a sound frame, a power spectrum of a frequency spectrum, and sound volume. The sound analyzing unit 12 outputs the calculated feature amount of the sound frame to the sleep state determining unit 13. Details of the sound analyzing unit 12 will be described later.

The sleep state determining unit 13 obtains the feature amount of the sound frame calculated by the sound analyzing unit 12 as input. The sleep state determining unit 13 calculates parameters used for determining a sleep state of the sound frame (hereinafter, referred to as the determination parameters) based on the feature amount of the sound frame. As the determination parameters, values obtained based on the feature amount of the sound frame calculated by the sound analyzing unit 12 are adopted. For example, the determination parameters are physical quantities representing frequency features, such as duration, the number of formats, and power spectrum variance of sound signals in a sound frame. The sleep state determining unit 13 holds values of the determination parameters pre-calculated for the characteristic sound A, the characteristic sound B, the characteristic sound C, and the breath sound (hereinafter, referred to as the comparison values). The sleep state determining unit 13 compares the values of determination parameters for the sound data with the comparison values of the characteristic sounds A to C and the comparison value of the breath sound to determine the sleep state of the sound frame. The sleep states include a "state with breathing" in which a sound frame includes a breath sound, that is, a subject is breathing. Further, the sleep states include a "breathing restored state" in which a sound frame includes any one of the characteristic sounds A to C, that is, a subject transitions from a respiratory arrest state to the breathing state. Furthermore, the sleep states include a "state without breathing" in which a sound frame does not include any one of the characteristic sounds A to C and breath sound, that is, the breathing of a subject remains stopped. The sleep state determining unit 13 outputs the sleep state of the sound frame to the apnea determining unit 14. Details of the sleep state determining unit 13 will be described later.

The apnea determining unit 14 obtains the sleep state of the sound frame from the sleep state determining unit 13 as input. The apnea determining unit 14 examines a history of sleep states of the sound frame to detect the apneic state of the subject. The apnea determining unit 14 outputs a detection result of the apneic state of the subject to the output unit 15. Details of the apnea determining unit 14 will be described later.

The output unit 15 is an interface to an external apparatus. The output unit 15 obtains a detection result of the apneic state of the subject as input. The output unit 15 outputs the detection result of the apneic state of the subject to any one or more of the network 5, the display 6, the speaker 7, and the secondary storage 8.

For example, if the apneic state of the subject is detected, the output unit 15 may inform the subject of the detection result of the apneic state by outputting an alarm indicating the detection result from the speaker 7. For example, the detection results of the apneic state of the subject in the sound frames, output from the output unit 15, may be stored in the secondary storage 8. For example, the detection results of the apneic state output from the output unit 15 may be displayed on the display 6. For example, the detection results of the apneic state of the subject, output from the output unit 15, may be transmitted via the network 5 to a specialized agency that examines sleep apneic syndrome.

<<A Configuration Example of the Sound Analyzing Unit>>

The sound analyzing unit 12 analyzes a sound frame to calculate a feature amount of the sound frame. In the first embodiment, the sound analyzing unit 12 calculates, for example, a power spectrum of a frequency as a feature amount of a sound frame.

Figure 3:
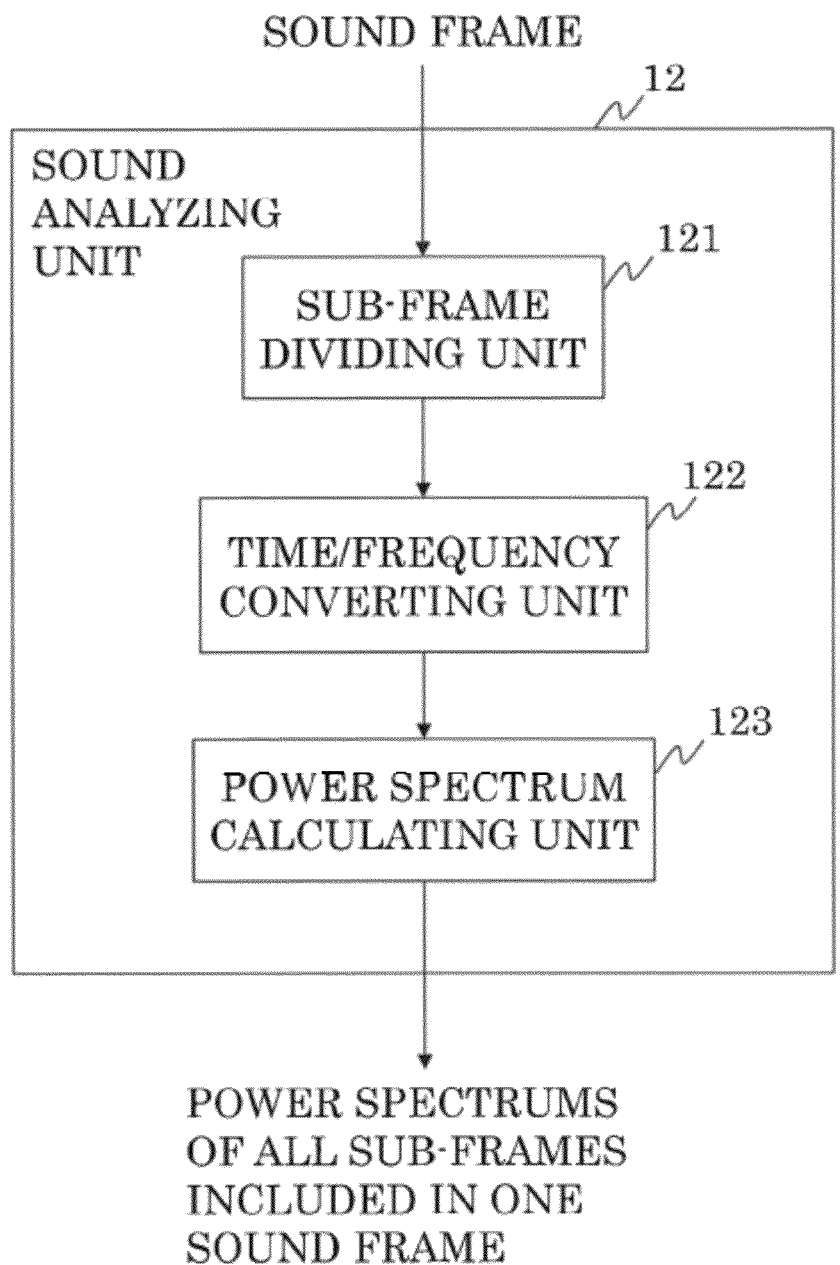
FIG. 3 is a diagram depicting a configuration example of the sound analyzing unit.

FIG. 3 is a diagram depicting a configuration example of the sound analyzing unit 12. The sound analyzing unit 12 includes a sub-frame dividing unit 121, a time/frequency converting unit 122, and a power spectrum calculating unit 123.

The sub-frame dividing unit 121 obtains a sound frame as input. The sub-frame dividing unit 121 divides a sound frame into sub-frames having a predetermined time length. In a case where a time length of a sound frame is two seconds, the sub-frame dividing unit 121 divides the sound frame into, for example, one hundred of equal parts, or sub-frames having 20 milliseconds as a predetermined time length. The sub-frame dividing unit 121 outputs the sound frame divided into the sub-frames to the time/frequency converting unit 122.

The time/frequency converting unit 122 obtains the sound frame divided into the sub-frames as input. The time/frequency converting unit 122 performs Fourier transformation on each sub-frame to convert a sound signal in a time domain into a signal in a frequency domain. When the time/frequency converting unit 122 finishes calculating frequency spectrums in all the sub-frames of one frame, the time/frequency converting unit 122 outputs the calculated frequency spectrums in all the sub-frames of one frame to the power spectrum calculating unit 123.

The power spectrum calculating unit 123 obtains the frequency spectrums in all the sub-frames of one frame, calculated by the time/frequency converting unit 122, as input. The power spectrum calculating unit 123 calculates a power spectrum of each sub-frame from the frequency spectrum of each sub-frame. When the power spectrum calculating unit 123 finishes calculating power spectrums in all the sub-frames of one frame, the power spectrum calculating unit 123 outputs the calculated power spectrums in all the sub-frames of one frame.

<<A Configuration Example of the Sleep State Determining Unit>>

The sleep state determining unit 13 calculates determination parameter values of a sound frame from a feature amount of the sound frame and compares the values with pre-calculated comparison values of the characteristic sounds A to C and the breath sound to determine the sleep state of the sound frame. In the first embodiment, the sleep state determining unit 13 calculates the values of the determination parameters based on information obtained from the power spectrums in all the sub-frames of one frame, received from the sound analyzing unit 12. In the first embodiment, as the determination parameters, duration, the number of formants, and variance of a fine structure power spectrum of a sound signal included in a sound frame are used.

Figure 4:
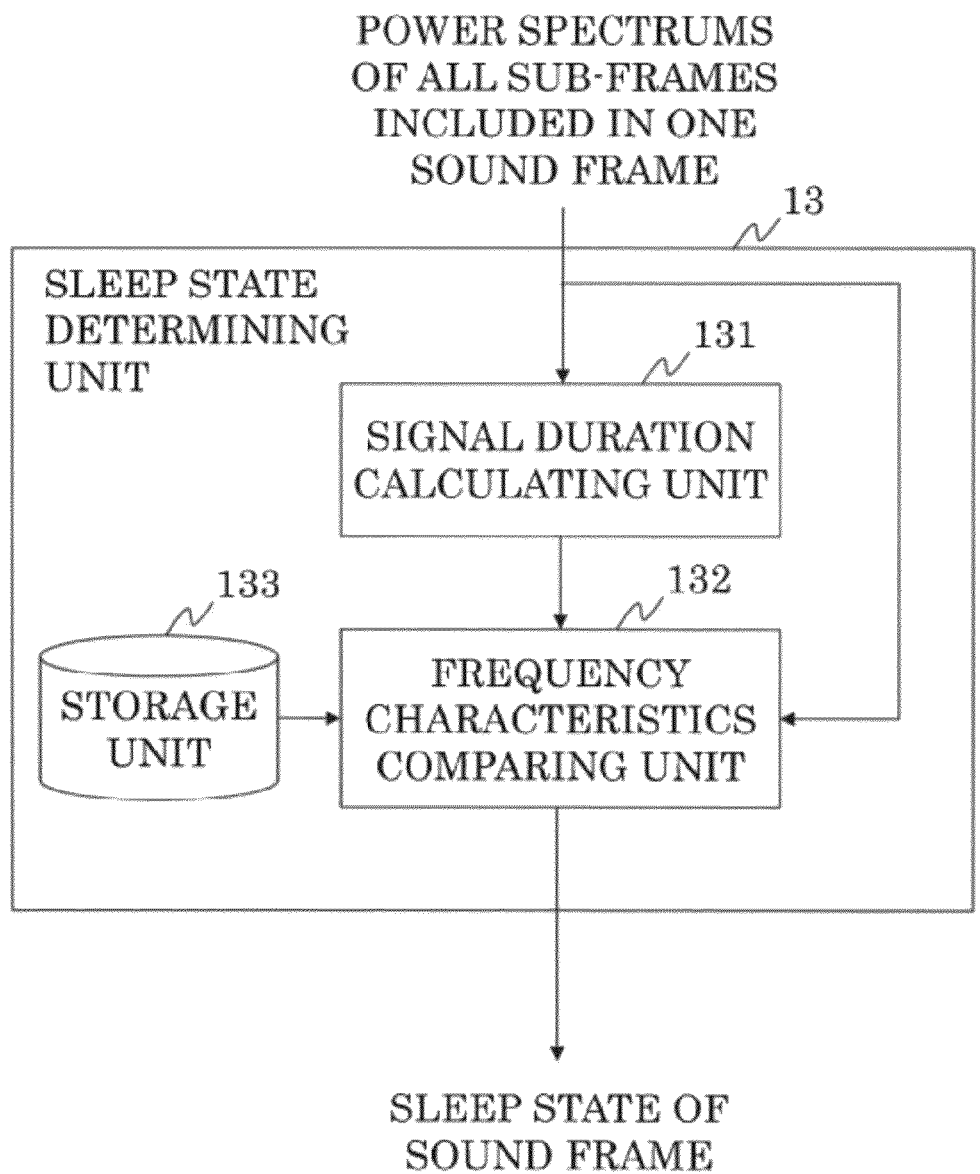
FIG. 4 is a diagram depicting a configuration example of the sleep state determining unit.

FIG. 4 is a diagram depicting a configuration example of the sleep state determining unit 13. The sleep state determining unit 13 includes a signal duration calculating unit 131, a frequency characteristics comparing unit 132, and a storage unit 133.

The storage unit 133 is created in a storage area of the main memory 19. The storage unit 133 stores therein the comparison values of the characteristic sound A, the characteristic sound B, the characteristic sound C, and the breath sound. The breath sound is a series of sounds generated by inhaling and exhaling, namely, a sound such as the breathing of a sleeping person or snoring. The same type of the comparison values of the characteristic sound A, the characteristic sound B, the characteristic sound C, and the and breath sound as a type of values of the determination parameters calculated from a received sound frame is employed. In the first embodiment, duration of the sound signals and information obtained from the frequency characteristics of the sound signals are used as determination parameters. Examples of the information obtained from the frequency characteristics of the sound signals include the number of formants and a variance value of a fine structure power spectrum.

Figure 5A:
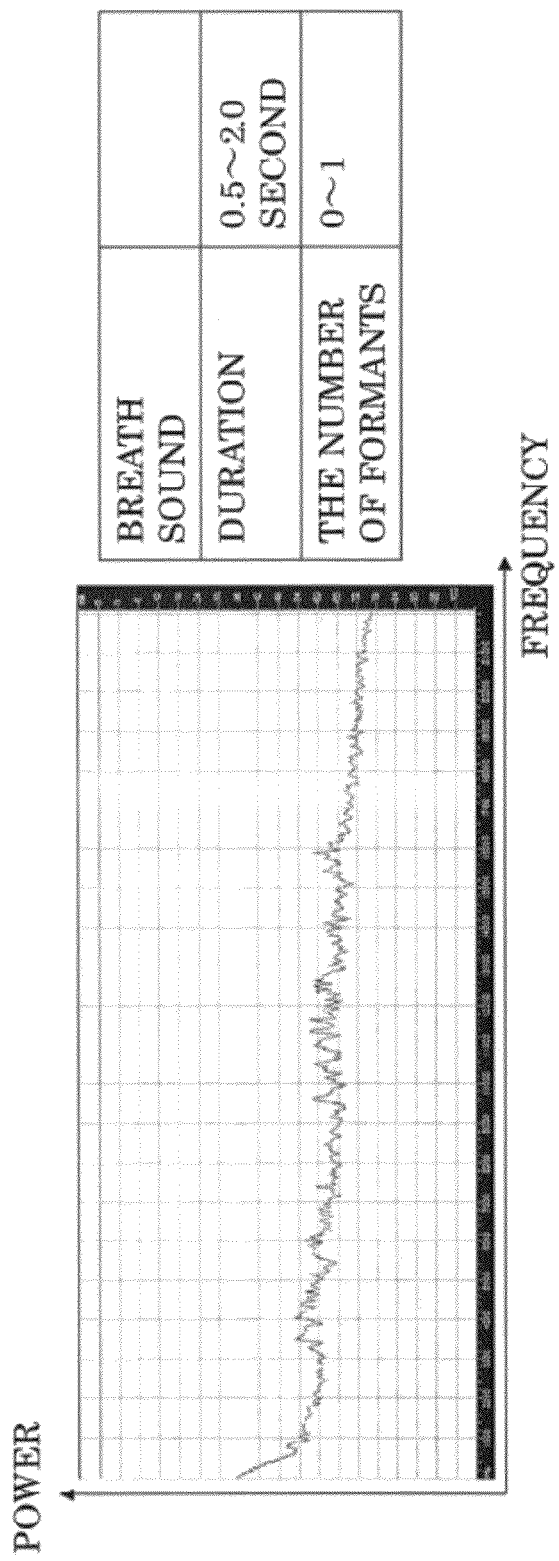
FIG. 5A illustrates an example of frequency characteristics of a breath sound.
Figure 5B:
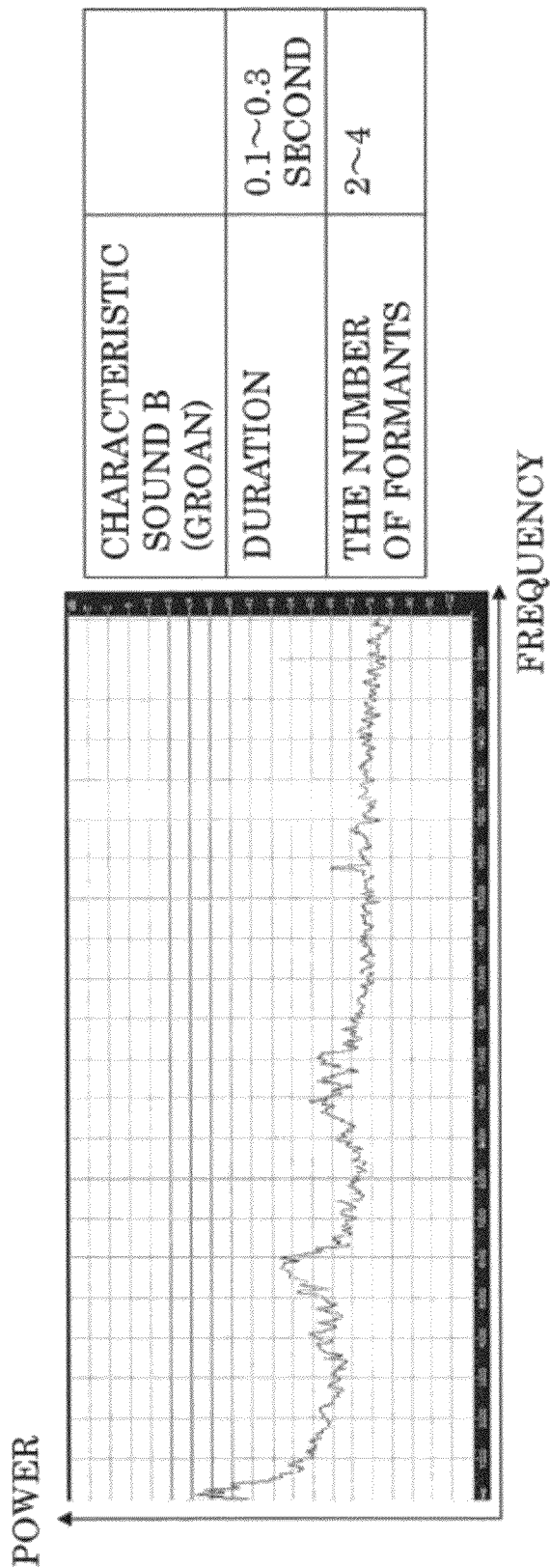
FIG. 5B illustrates an example of frequency characteristics of the characteristic sound B.
Figure 5C:
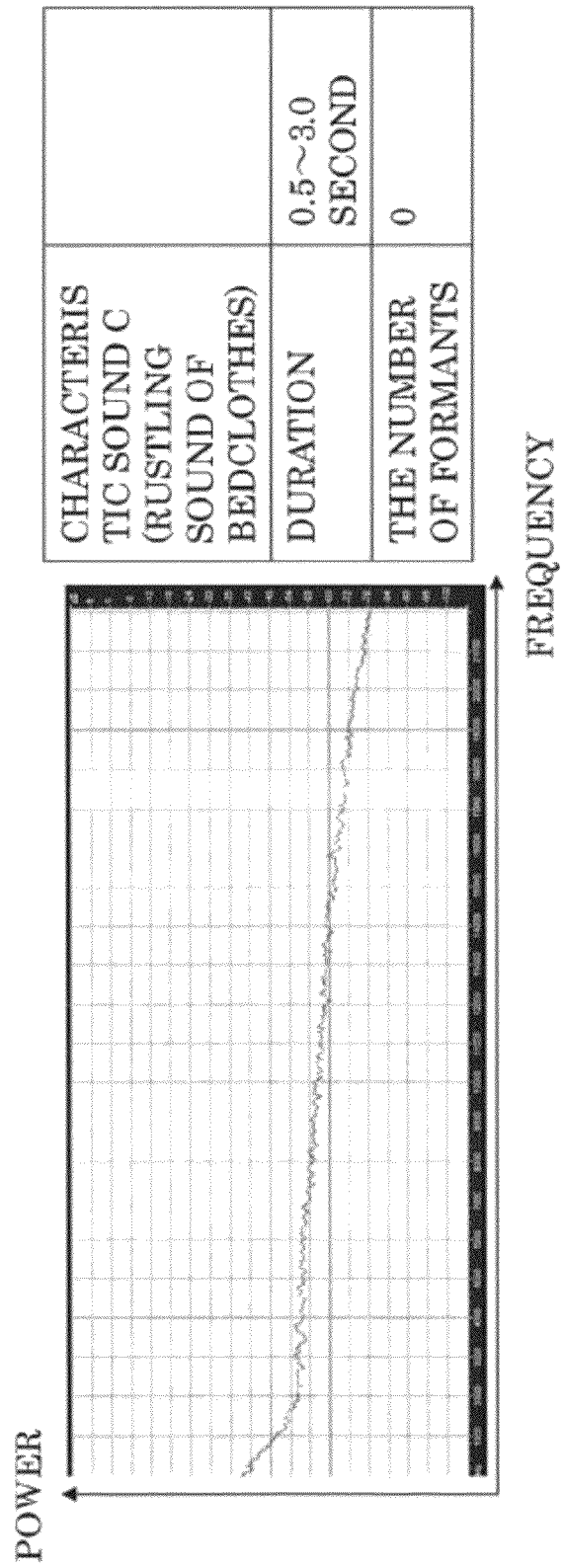
FIG. 5C illustrates an example of frequency characteristics of the characteristic sound C.

FIG. 5A, FIG. 5B, and FIG. 5C illustrate examples of the frequency characteristics of the breath sound, the characteristic sound B, and the characteristic sound C, respectively. Further, in the examples illustrated in FIG. 5A, FIG. 5B, and FIG. 5C, duration, the number of formants, and variance of a fine structure power spectrum of sound signals are depicted as the information obtained from the frequency characteristics, namely, the determination parameters.

FIG. 5A illustrates an example of frequency characteristics of a breath sound. In a graph depicting a relationship between a frequency and a power spectrum of a breath sound, although there are no definite peaks, slight jaggedness is observed. A range of the duration of the sound signal of the breath sound is 0.5 to 2.0 seconds. A range of the number of formants of the breath sound is 0 to 1. As illustrated in FIG. 5A, since the graph depicting the relationship between the frequency and the power spectrum of the breath sound has the slight jaggedness, the variance of a fine structure power spectrum of the breath sound, which indicates the variation of power spectrums from an average, may take a certain range of values.

The relationship between a frequency and a power spectrum of the characteristic sound A, namely, a short breath sound is similar to the graph illustrated in FIG. 5A, depicting the relationship between the frequency and the power spectrum of the breath sound. The duration of the sound signal of the characteristic sound A is 0.2 to 0.3 seconds. Further, since the graph depicting the relationship between the frequency and the power spectrum of the characteristic sound A is similar to the graph illustrated in FIG. 5A, depicting the relationship between the frequency and the power spectrum of the breath sound, the range of the number of formants included in the characteristic sound A is 0 to 1. Furthermore, the variance of the fine structure power spectrum of the characteristic sound A may also take values approximate to the variance of the fine structure power spectrum of the breath sound.

FIG. 5B illustrates an example of frequency characteristics of the characteristic sound B, namely, a groan. A range of the duration of the sound signal of the characteristic sound B is 0.1 to 0.3 seconds. As illustrated in FIG. 5B, in the graph depicting the relationship between the frequency and the power spectrum of the characteristic sound B, two or three definite peaks are observed. A range of the number of formants included in the characteristic sound B is two to four. Comparing the graph illustrated in FIG. 5B, which depicts the relationship between the frequency and the power spectrum of the characteristic sound B, with the graph illustrated in FIG. 5A, which depicts the relationship between the frequency and the power spectrum of the breath sound, it is seen that fluctuations of the values of the power spectrum in the graph of the characteristic sound B are greater than those in the graph of the breath sound. Therefore, the values of the variance of the fine structure power spectrum of the characteristic sound B are greater than the values of the variance of the fine structure power spectrum of the breath sound.

FIG. 5C illustrates an example of frequency characteristics of the characteristic sound C, namely, a sound of a body movement of a subject. A range of the duration of the sound signal of the characteristic sound C is 0.5 to 3.0 seconds. As illustrated in FIG. 5C, in the graph depicting the relationship between the frequency and the power spectrum of the characteristic sound C, no definite peaks and no significant fluctuations are observed. Since the graph depicting the relationship between the frequency and the power spectrum of the characteristic sound C has no definite peaks, the number of formants included in the characteristic sound C is 0. Comparing the graph illustrated in FIG. 5C, which depicts the relationship between the frequency and the power spectrum of the characteristic sound C, with the graph illustrated in FIG. 5A, which depicts the relationship between the frequency and the power spectrum of the breath sound, it is seen that fluctuations of the values of the power spectrum in the graph of the characteristic sound C are smaller than those in the graph of the breath sound. Therefore, the values of the variance of the fine structure power spectrum of the characteristic sound C are smaller than the values of the variance of the fine structure power spectrum of the breath sound.

FIG. 6 is an example of a table in which the frequency characteristics of the breath sound, the characteristic sound A, the characteristic sound B, and the characteristic sound C are organized. In the example illustrated in FIG. 6, a range of variance of a fine structure power spectrum is classified into "great," "medium" and "small" beforehand, and a possible range of the values of the variance of the fine structure power spectrum of the breath sound is fixed at "medium."

Since the graph (not shown) depicting the relationship between the frequency and the power spectrum of the characteristic sound A is similar to the graph (FIG. 5A) depicting the relationship between the frequency and the power spectrum of the breath sound, the values of the variance of the fine structure power spectrum are also similar. Therefore, the values of the variance of the fine structure power spectrum of the characteristic sound A are, similarly to those of the breath sound, "medium."

Comparing the graph (FIG. 5B) depicting the relationship between the frequency and the power spectrum of the characteristic sound B with the graph (FIG. 5A) depicting the relationship between the frequency and the power spectrum of the breath sound, it is seen that the variance of the values of the power spectrum in the graph of the characteristic sound B is greater than the variance of the values of the power spectrum of the breath sound. Therefore, the values of the variance of the fine structure power spectrum of the characteristic sound B are "great."

Comparing the graph (FIG. 5C) depicting the relationship between the frequency and the power spectrum of the characteristic sound C with the graph (FIG. 5A) depicting the relationship between the frequency and the power spectrum of the breath sound, it is seen that the variance of the values of the power spectrum in the graph of the characteristic sound C is smaller than the variance of the values of the power spectrum of the breath sound. Therefore, the values of the variance of the fine structure power spectrum of the characteristic sound C are "small."

Turning back to FIG. 4, the signal duration calculating unit 131 obtains the power spectrum of all the sub-frames of one frame as input. The signal duration calculating unit 131 calculates duration of a sound signal included in the sound frame from the power spectrum of all the sub-frames of one frame.

Figure 7:
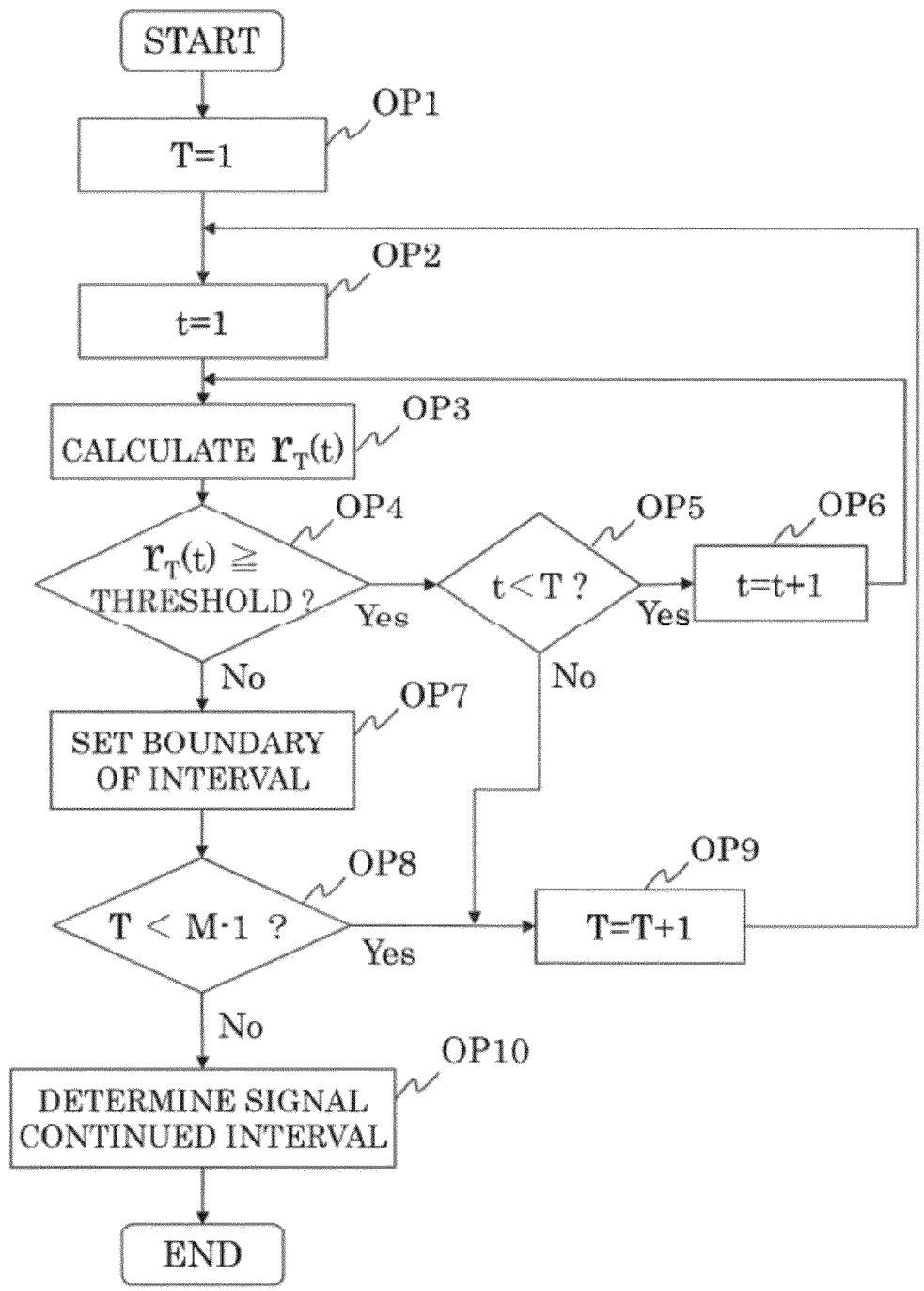
FIG. 7 illustrates an example of a flow of the sound signal duration calculating processing performed by the signal duration calculating unit.

FIG. 7 illustrates an example of a flow of the sound signal duration calculating processing performed by the signal duration calculating unit 131. In the example illustrated in FIG. 7, the signal duration calculating unit 131 determines a correlation coefficient $r_T(t)$ between a sound signal in a sub-frame T and a sound signal in a sub-frame T-t, previous to the sub-frame T, to calculate the duration of the sound signal. The number of sub-frames in a sound frame is fixed at M (M being a natural number, not including 0).

When the signal duration calculating unit 131 receives the power spectrums of all the sub-frames of the sound frame from the sound analyzing unit 12, the signal duration calculating unit 131 starts the sound signal duration calculating processing.

The signal duration calculating unit 131 sets an initial value of a variable T indicating a sub-frame, to 1 (OP1). A range of the variable T, indicating the sub-frames, is 1≤T≤M−1.

Next, the signal duration calculating unit 131 sets an initial value of a variable t indicating the number of sub-frames previous to the sub-frame T, to 1 (OP2). A range of the variable t, indicating the number of sub-frames previous to the sub-frame T, is 1≤t≤T.

The signal duration calculating unit 131 calculates a correlation coefficient $r_T(t)$ between a sound signal included in the sub-frame T and a sound signal included in the sub-frame T-t by using the following expression 1 (OP3). Hereinafter, the correlation coefficient $r_T(t)$ between the sound signal included in the sub-frame T and the sound signal included in the sub-frame T-t is referred to as the "the correlation coefficient $r_T(t)$ between the sub-frame T and the sub-frame T-t."

$$r_T(t) = \frac{\sum_{i=0}^{N-1}(P_T(i) - \overline{P_T})\sum_{i=0}^{N-1}(P_{T-t}(i) - \overline{P_{T-t}})}{\sqrt{\sum_{i=0}^{N-1}(P_T(i) - \overline{P_T})^2}\sqrt{\sum_{i=0}^{N-1}(P_{T-t}(i) - \overline{P_{T-t}})^2}}$$

Expression 1

$(t = 1, 2 \ldots K)$ $r_T(t)$: The correlation coefficient between the sound signal in the sub-frame T and the sound signal in the sub-frame T-t
$P_T(i)$: Power of an i-th frequency in the sub-frame T
$\overline{P_T}$: An average of power of each frequency in the sub-frame T
N: The total number of frequency bands
K: The number of sub-frames with which correlations are calculated (1≤K≤T)

The signal duration calculating unit 131 determines whether or not a calculated value of the correlation coefficient $r_T(t)$ between the sub-frame T and the sub-frame T-t is equal to or greater than a predetermined threshold value (OP4). For example, the predetermined threshold value is 0.7.

If the calculated value of the correlation coefficient $r_T(t)$ between the sub-frame T and the sub-frame T-t is equal to or greater than the threshold value (OP4: Yes), the sound signal included in the sub-frame T and the sound signal included in the sub-frame T-t are deemed to be the same sound signal. That is, if the value of the correlation coefficient $r_T(t)$ between the sub-frame T and the sub-frame T-t is equal to or greater than the threshold value, it is indicated that the sound signal continues from the sub-frame T-t to the sub-frame T.

If the value of the correlation coefficient $r_T(t)$ between the sub-frame T and the sub-frame T-t is equal to or greater than the threshold value (OP4: Yes), then the signal duration calculating unit 131 determines whether or not t is smaller than the variable T (OP5). That is, the signal duration calculating unit 131 determines whether or not there is a sub-frame T-t, which is previous to the sub-frame T.

If the variable t is smaller than the variable T (OP5: Yes), it is indicated that there is, prior to the sub-frame T, a sub-frame T-t whose correlation coefficient $r_T(t)$ with respect to the sub-frame T has not been determined. That is, it is indicated that a process for determining the correlation coefficient $r_T(t)$ with respect to the sub-frame T is continuing.

If the variable t is smaller than the variable T (OP5: Yes), the signal duration calculating unit 131 sets the variable t to t+1 (OP6).

If the variable t is equal to or greater than the variable T (OP5: No), it is indicated that for all the sub-frames previous to the sub-frame T, correlation coefficients $r_T(t)$ with respect to the sub-frame T have been determined. That is, it is indicated that for the sub-frame T, the process for determining the correlation coefficients $r_T(t)$ ends. Then, the processing proceeds to OP9 and a process for determining a correlation coefficient $r_T(t)$ with respect to a sub-frame T+1 next to the sub-frame T starts.

If the calculated value of the correlation coefficient $r_T(t)$ between the sub-frame T and the sub-frame T-t is smaller than the threshold value (OP4: No), the sound signal included in the sub-frame T and the sound signal included in the sub-frame T-t are deemed to be different sound signals. If the calculated value of the correlation coefficient $r_T(t)$ between the sub-frame T and the sub-frame T-t is smaller than the threshold value, the signal duration calculating unit 131 ends the process for determining the correlation coefficients $r_T(t)$ between the sub-frame T and the sub-frames previous to the sub-frame T.

The signal duration calculating unit 131 sets a boundary between a sub-frame T-t and a sub-frame T-t+1 as a boundary of a continuing interval of a sound signal (OP7). Hereinafter, the continuing interval of a sound signal is also simply referred to as the "interval."

The signal duration calculating unit 131 then determines whether or not the variable T is smaller than M−1 (OP8). That is, the signal duration calculating unit 131 determines whether or not for all the sub-frames T included in the sound frame, the process for determining correlation coefficients $r_T(t)$ between the sub-frames T and the sub-frames T-t previous to the sub-frames T has ended.

If the variable T is smaller than M−1 (OP8: Yes), it is indicated that for all the sub-frames T included in the sound frame, a process for determining the correlation coefficients $r_T(t)$ between the sub-frames T and the sub-frames T-t previous to the sub-frame T has not ended. If the variable T is smaller than M−1, the signal duration calculating unit 131 sets the variable T to T+1 (OP9). Then, the processing returns to OP2, and for a next sub-frame T, a process for determining correlation coefficients $r_T(t)$ between the sub-frame T and the sub-frames previous to the sub-frame T is performed.

If the variable T is equal to or greater than M−1 (OP8: No), it is indicated that for all the sub-frames T included in the sound frame, the process for determining the correlation coefficients $r_T(t)$ between the sub-frames T and the sub-frames T-t previous to the sub-frames T has ended. The signal duration calculating unit 131 determines, based on the boundaries of the intervals determined in OP7, intervals in which sound signals continue, and calculates duration of the sound signal included in each interval (OP10). The signal duration calculating unit 131 counts the number of sub-frames included in each interval and calculates duration of the sound signal in each interval. For example, assuming that a time length of a sound frame is two seconds and a time length of a sub-frame is 20 milliseconds, which is one-hundredth of the sound frame, if one interval includes five sub-frames, duration of a sound signal in the interval is calculated as 0.1 seconds.

Figure 8:
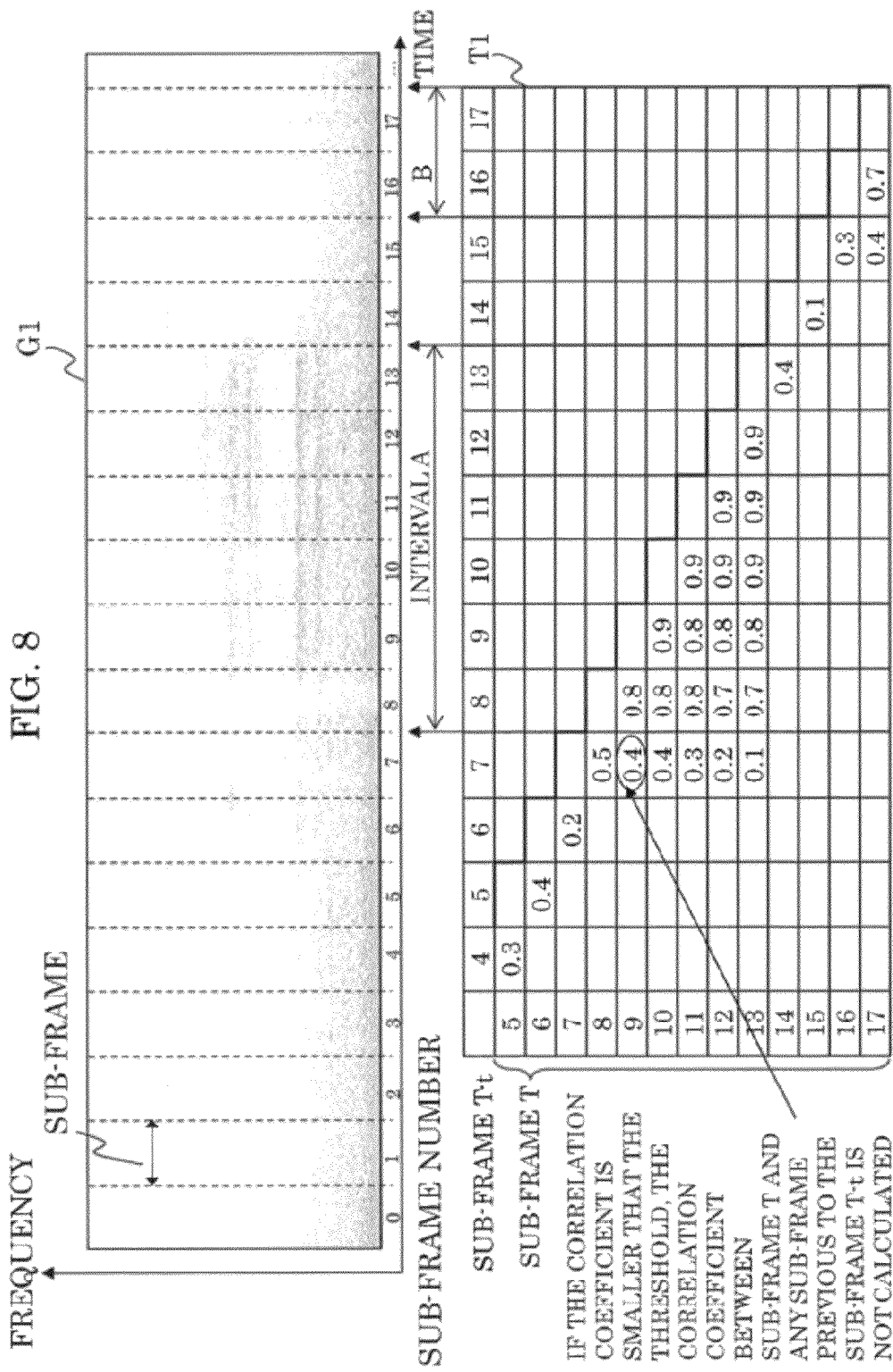
FIG. 8 illustrates diagrams depicting the sound signal duration calculating processing.

FIG. 8 illustrates diagrams depicting the sound signal duration calculating processing in FIG. 7. In FIG. 8, a first sub-frame in a sound frame is indicated as sub-frame 0, and along a temporal axis, following sub-frames are indicated as sub-frame 1, sub-frame 2, and so on. In the example illustrated in FIG. 8, sub-frame 0 to sub-frame 17 of the sound frame are seen.

In the example illustrated in FIG. 8, it is assumed that a characteristic sound is included in sub-frame 8 through sub-frame 13. Further, a table T1 indicates an example of a result obtained by performing the processing illustrated in FIG. 7 on the sound signal illustrated in FIG. 8. That is, the table T1 indicates a part of the result obtained by performing the processing for determining correlation coefficients $r_T(t)$ between sub-frames T and sub-frames T-t previous to the sub-frame T by t for all the sub-frames T included in the sound frame including the sound signal of the graph G1. In the table T1, the leftmost column represents values of the variables T indicating sub-frames, and the top row represents values of the sub-frames T-t, previous to the sub-frame T by t. Values in coordinates (T, T-t) of the table T1 represent values of the correlation coefficients $r_T(t)$ between the sub-frames T and the sub-frames T-t, previous to the sub-frames T by t.

For example, the table T1 is created in the following manner in accordance with the flow illustrated in FIG. 7.

First, the signal duration calculating unit 131 sets T to 1 and t to 1 (FIG. 7: OP1 and OP2). The signal duration calculating unit 131 determines a correlation coefficient $r_T(t)$ between sub-frame 1 and sub-frame 0 (FIG. 7: OP3). The signal duration calculating unit 131 records a value of the correlation coefficient $r_T(t)$ between sub-frame 1 and sub-frame 0 on the coordinates (1, 0) of the table T1. If the value of the correlation coefficient $r_T(t)$ between sub-frame 1 and sub-frame 0 is equal to or greater than 0.7 being a predetermined threshold value (FIG. 7: OP4, Yes), the signal duration calculate unit 131 determines whether or not t is smaller than T (FIG. 7: OP5). Since t=1 and T=1, that is, t is equal to T (FIG. 7: OP5, No), the signal duration calculating unit 131 sets T to T+1=1+1=2 (FIG. 7: OP9). The signal duration calculating unit 131 then sets t to 1 (FIG. 7: OP2), and determines a correlation coefficient $r_T(t)$ between sub-frame 2 and sub-frame 1 (FIG. 7: OP3).

Thereafter, the signal duration calculating unit 131 performs the processes of OP2 to OP9 in FIG. 7 to provide the table T1 illustrated in FIG. 8.

In the process in OP10 of FIG. 7, for all the sub-frames T included in the sound frame, if the correlation coefficients $r_T(t)$ between the sub-frames T and the sub-frames T-t previous to the sub-frames T are calculated, the signal duration calculating unit 131 determines a continuing interval of a sound signal. In the example illustrated in FIG. 8, a boundary of the continuing interval of the sound signal is determined between coordinates smaller than "0.7" and coordinates equal to or greater than "0.7" in the table T1. The signal duration calculating unit 131 detects an interval A including sub-frame 8 through sub-frame 13 and an interval B including sub-frame 16 and sub-frame 17.

The signal duration calculating unit 131 calculates duration of the sound signal in each of the interval A and the interval B. In the example illustrated in FIG. 8, it is assumed that a time length of the sub-frame is 0.02 seconds. Therefore, in the example illustrated in FIG. 8, the duration of the interval A is 0.12 seconds (0.02 seconds×6). The duration of the interval B is 0.04 seconds (0.02 seconds×2).

The signal duration calculating unit 131 outputs a continuing interval of each sound signal included in the sound frame and the duration of the sound signal in the continuing interval of the sound signal to the frequency characteristics comparing unit 132.

The frequency characteristics comparing unit 132 obtains power spectrums of all the sub-frames of one frame, a continuing interval of a sound signal included in the sound frame, and duration of the continuing interval of each sound signal as input. The frequency characteristics comparing unit 132 extracts from the sound frame only a continuing interval of a sound signal, duration of which is equal to or greater than a predetermined value. The "duration of the sound signal is equal to or greater than a predetermined value" means that, for example, duration of a sound signal included in a sound frame is 0.1 seconds or longer because a value of duration of a sound signal of the characteristic sound C is 0.1 to 0.3 seconds.

The frequency characteristics comparing unit 132 calculates an average power spectrum in the extracted interval. The frequency characteristics comparing unit 132 separates the sound signal in the extracted interval into an envelope part and a fine structure part by using a known method such as cepstrum analysis from the average power spectrum of the extracted interval. The frequency characteristics comparing unit 132 calculates a power spectrum of the separated envelope part. The frequency characteristics comparing unit 132 counts the number of local maximum values (peaks) of the power spectrum of the envelope part and defines the number as the number of formants. At this time, minute peaks may be excluded from the number of formants.

The frequency characteristics comparing unit 132 calculates variance of a power spectrum of the fine structure of the sound signal in the extracted interval by using the following expression 2.

$$S^2 = \frac{1}{N}\sum_{i=0}^{N-1}\{\overline{G} - G(i)\}^2 \qquad \text{Exression 2}$$

S: A value of variance
N: The total number of frequency bands
$\overline{G}$: An average value of fine structure power spectrums
G(i): A fine structure power spectrum of an i-th frequency In the foregoing manner, the frequency characteristics comparing unit 132 calculates the number of formants and a value of variance of a fine structure power spectrum for each interval in which duration of a sound signal included in a sound frame is equal to or greater than a predetermined value.

For example, in the case of the sound signal as illustrated in FIG. 8, since the duration of the interval A is 0.12 seconds and the duration of the interval B is 0.04 seconds, only the duration of the interval A is equal to or greater than a predetermined value (e.g., 0.1 seconds). Therefore, in the case of the sound signal as illustrated in FIG. 8, the frequency characteristics comparing unit 132 extracts the interval A. The frequency characteristics comparing unit 132 calculates the number of formants and a value of variance of a fine structure power spectrum of a sound signal included in the extracted interval A.

The frequency characteristics comparing unit 132 compares the number of formants and the value of the variance of the fine structure power spectrum of the sound signal in each extracted interval, with a range of the comparison values of the number of formants and the variance of the fine structure power spectrum in each of the characteristic sounds A to C and the breath sound. Hereinafter, the number of formants and a value of variance of a fine structure power spectrum of a sound signal included in an interval are referred to as the "sleep state determination parameters."

If values of the sleep state determination parameters in the extracted interval are within the range of the comparison values of the sleep state determination parameters of the characteristic sounds A to C, the frequency characteristics comparing unit 132 detects the fact that the interval includes a characteristic sound. The fact that the interval includes a characteristic sound means that a sound frame having the interval includes a characteristic sound. A state in which a sound frame includes a characteristic sound is referred to as the "breathing restored state," where the subject transitions from the respiratory arrest state to the breathing state. That is, if at least one of extracted intervals includes a characteristic sound, the frequency characteristics comparing unit 132 determines the sleep state of the sound frame as the "breathing restored state."

If the values of the sleep state determination parameters in the extracted interval are within a range of the comparison values of the sleep state determination parameters of the breath sound, the frequency characteristics comparing unit 132 detects the fact that the interval includes a breath sound.

If any one of the extracted intervals does not include a characteristic sound and at least one of the extracted intervals includes a breath sound, the frequency characteristics comparing unit 132 determines the sleep state of the sound frame as the "state with breathing."

If any one of the extracted intervals does not include either of a characteristic sound and a breath sound, the frequency characteristics comparing unit 132 detects the fact that the sound frame does not include either of a characteristic sound and a breath sound. If the sound frame does not include either of a characteristic sound and a breath sound, it is presumed that the subject is in a respiratory arrest state. The state in which it is presumed that the subject is in a respiratory arrest state is defined as the "state without breathing." That is, if any value of the sleep state determination parameters of the extracted intervals is not within a range of the comparison values of the sleep state determination parameters of any one of the characteristic sounds A to C and the breath sound, the frequency characteristics comparing unit 132 determines the sleep state of the sound frame as the "state without breathing."

For example, in the case of the sound signal in the example illustrated in FIG. 8, since the fact that the interval A includes a characteristic sound is detected, the sleep state of the sound signal in the example illustrated in FIG. 8 is determined as the "breathing restored state."

The frequency characteristics comparing unit 132 outputs any one of the "breathing restored state," the "state with breathing," and the "state without breathing" to the apnea determining unit 14 as a determination result of the sleep state of the sound frame.

Figure 9:
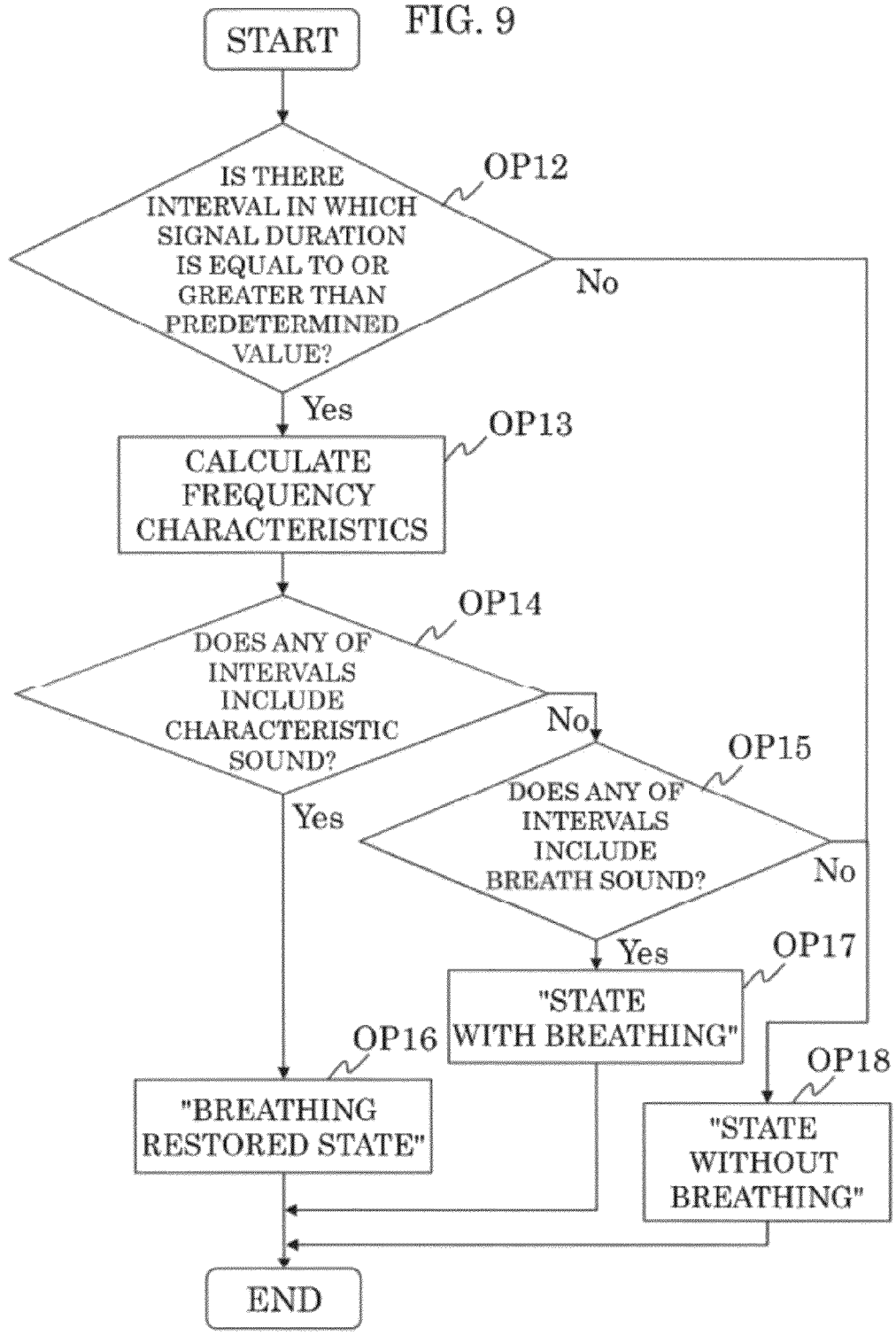
FIG. 9 is an example of a flow of processing for determining the sleep state of a sound frame, performed by the frequency characteristics comparing unit.

FIG. 9 is a diagram depicting an example of a flow of processing for determining the sleep state of a sound frame, performed by the frequency characteristics comparing unit 132.

When the frequency characteristics comparing unit 132 receives power spectrums of all the sub-frames of one frame, a continuing interval of a sound signal included in the sound frame, and duration of the continuing interval of each sound signal, the frequency characteristics comparing unit 132 starts the processing for determining the sleep state of the sound frame.

The frequency characteristics comparing unit 132 determines whether or not the sound frame includes an interval in which the duration of the sound signal is equal to or greater than a predetermined value (OP12). For example, the frequency characteristics comparing unit 132 determines whether or not the duration of the sound signal is 0.1 seconds or longer for each interval included in the sound frame.

If the interval in which the duration of the sound signal is equal to or greater than a predetermined value is included in the sound frame (OP12: Yes), the frequency characteristics comparing unit 132 extracts the interval in which the duration of the sound signal is equal to or greater than the predetermined value. The frequency characteristics comparing unit 132 calculates frequency characteristics of the sound signal in the duration for each extracted interval (OP13). The calculated frequency characteristics are the number of formants, variance of a fine structure power spectrum, and the like. The frequency characteristics are calculated based on power spectrums of sub-frames included in each interval.

The frequency characteristics comparing unit 132 compares the values of the frequency characteristics of the sound signal in each extracted interval, with a range of the comparison values of the frequency characteristics of the characteristic sounds A to C, stored in the storage unit 133, and determines whether or not any one of the extracted intervals includes a characteristic sound (OP14).

If at least one of the extracted intervals includes a characteristic sound (OP14: Yes), the frequency characteristics comparing unit 132 determines the sleep state of the sound frame as the "breathing restored state" (OP16). The frequency characteristics comparing unit 132 outputs the "breathing restored state" as the sleep state of the sound frame, and then ends the processing for determining the sleep state of the sound frame.

If any one of the extracted intervals does not include a characteristic sound (OP14: No), the frequency characteristics comparing unit 132 determines whether or not at least one of the extracted intervals includes a breath sound (OP15).

If at least one of the extracted intervals includes a breath sound (OP15; Yes), the frequency characteristics comparing unit 132 determines the sleep state of the sound frame as the "state with breathing" (OP17). The frequency characteristics comparing unit 132 outputs the "state with breathing" as the sleep state of the sound frame, and then ends the processing for determining the sleep state of the sound frame.

If a sound frame does not include an interval in which duration of the sound signal is equal to or greater than a predetermined value (OP12: No), the frequency characteristics comparing unit 132 determines the sleep state of the sound frame as the "state without breathing" (OP18). Further, if any one of the extracted intervals does not include either of a characteristic sound and a breath sound (OP15; No), the frequency characteristics comparing unit 132 determines the sleep state of the sound frame as the "state without breathing" (OP18). The frequency characteristics comparing unit 132 outputs the "state without breathing" as the sleep state of the sound frame, and then ends the processing for determining the sleep state of the sound frame.

<<A Configuration Example of the Apnea Determining Unit>>

The apnea determining unit 14 obtains any one of the "state with breathing," the "state without breathing," and the "breathing restored state," which are the sleep states of the sound frame, as input. The apnea determining unit 14 detects an apneic state of the subject based on a history of the sleep states of the sound frame.

Figure 10:
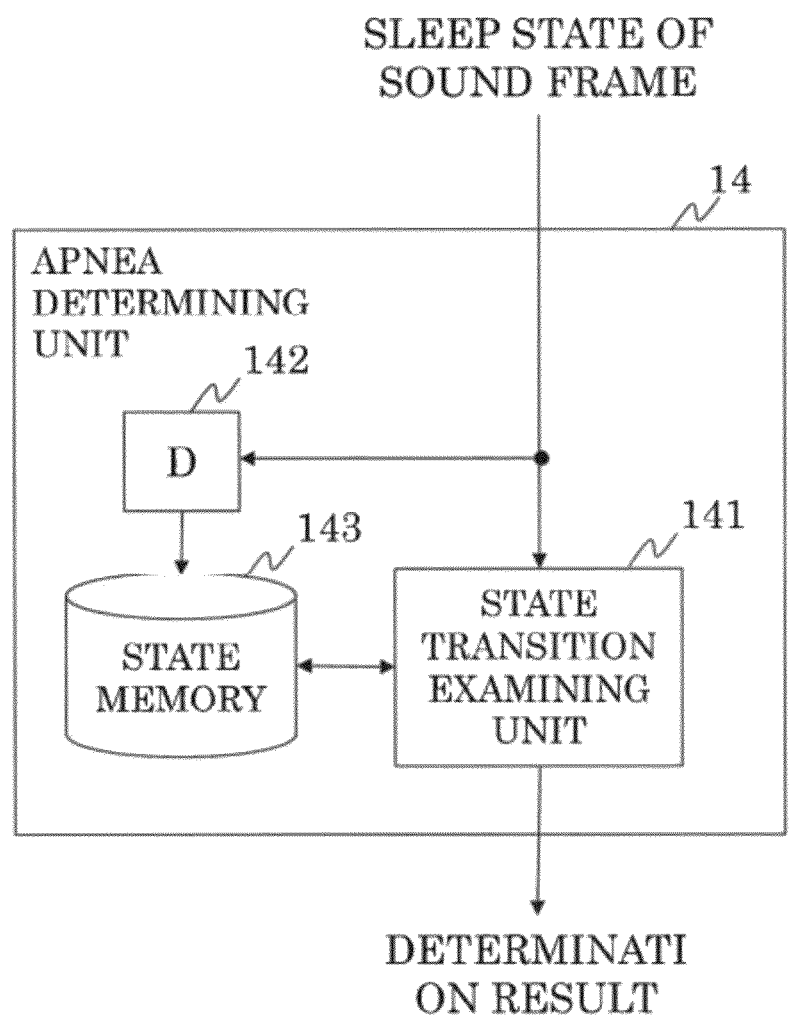
FIG. 10 is a diagram depicting a configuration example of the apnea determining unit.

FIG. 10 is a diagram depicting a configuration example of the apnea determining unit 14. The apnea determining unit 14 includes a state transition examining unit 141, a delay element 142, and state memory 143.

The input sleep state of the sound frame is input to the state transition examining unit 141 and the delay element 142. The delay element 142 stores the sleep state of the sound frame into the state memory 143 after a delay of one-frame processing. That is, when the sleep state of the sound frame is input, the delay element 142 temporarily holds the sleep state, and when a sleep state of a next sound frame is input, the delay element 142 stores the sleep state of the preceding sound frame into the state memory 143.

In the state memory 143, the sleep states of the sound frames are stored in chronological order. In the state memory 143, for example, a history of the sleep states of a few minutes of the sound frame is stored in reverse chronological order from a current sound frame.

The state transition examining unit 141 obtains the sleep state of the sound frame as input. If the sleep state of the sound frame is the "breathing restored state," the state transition examining unit 141 examines in reverse chronological order the history of the sleep states of the sound frame stored in the state memory 143.

Figure 11:
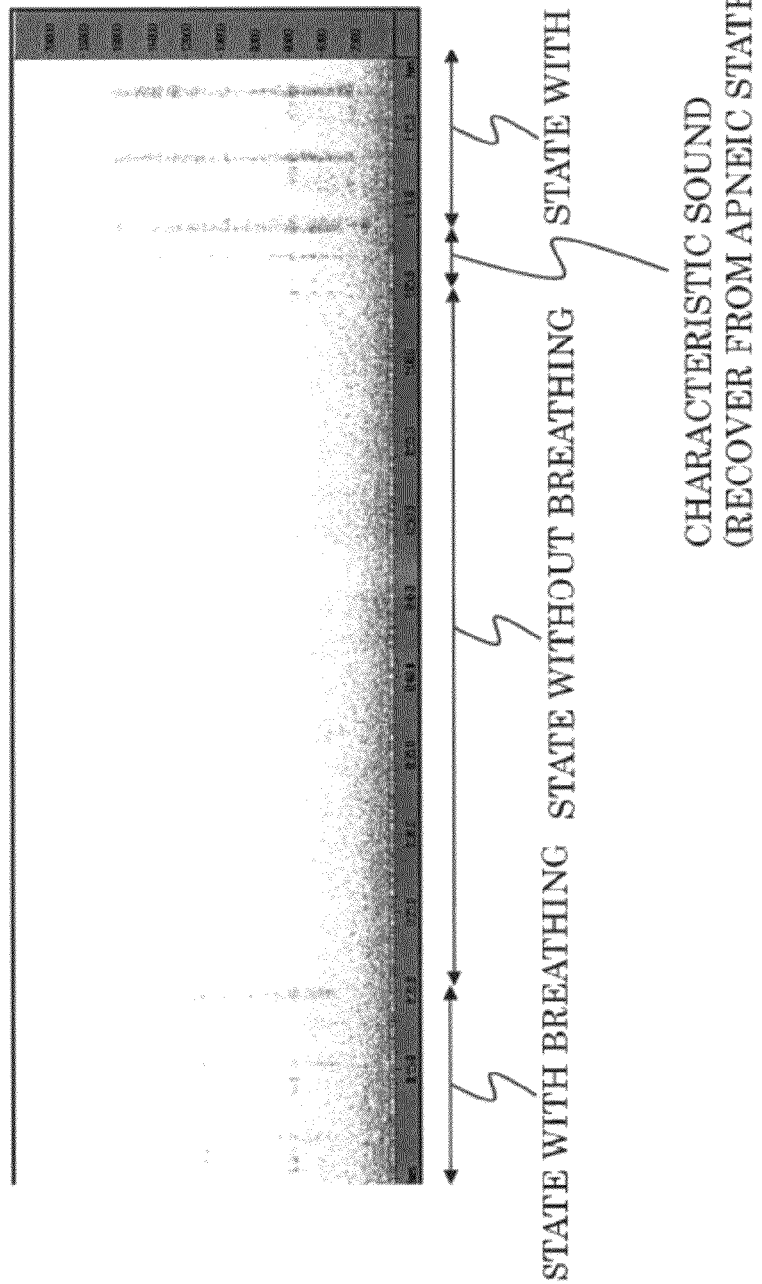
FIG. 11 is a graph depicting an example of breathing of a patient of sleep apnea syndrome during sleep.

FIG. 11 is a graph depicting an example of breathing of a patient of sleep apnea syndrome during sleep. The patient of sleep apnea syndrome, during sleep, transitions from a breathing state to a respiratory arrest state. After a predetermined duration (e.g., about ten seconds to two minutes) with the respiratory arrest state has passed, a characteristic sound occurs, and the patient of sleep apnea syndrome starts breathing. That is, in the patient of sleep apnea syndrome during sleep, after the "state with breathing," the "state without breathing" continues for a predetermined duration, and then the patient transitions to the "breathing restored state."

The state transition examining unit 141 detects the apneic state of the subject by employing the fact that the sleep state of the patient of sleep apnea syndrome transitions from the "state with breathing," through a predetermined duration of the "state without breathing," to the "breathing restored state" in this order. That is, if the sleep state of the sound frame is the "breathing restored state," the state transition examining unit 141 examines the history of the sleep states of the sound frame, stored in the state memory 143. The state transition examining unit 141 examines whether or not the "state without breathing" continues for a predetermined duration before a current sound frame and the "state with breathing" exists before the "state without breathing." As a result of the examination, if the sleep state of the subject transitions from the "state with breathing," through a predetermined duration of the "state without breathing," to the "breathing restored state" in this order, the state transition examining unit 141 detects the fact that the subject is in an apneic state.

If the sleep state of the sound frame is the "state with breathing" and the "state without breathing," the state transition examining unit 141 ends the processing. The state transition examining unit 141 outputs the detection result of the apneic state to the output unit 15.

Figure 12:
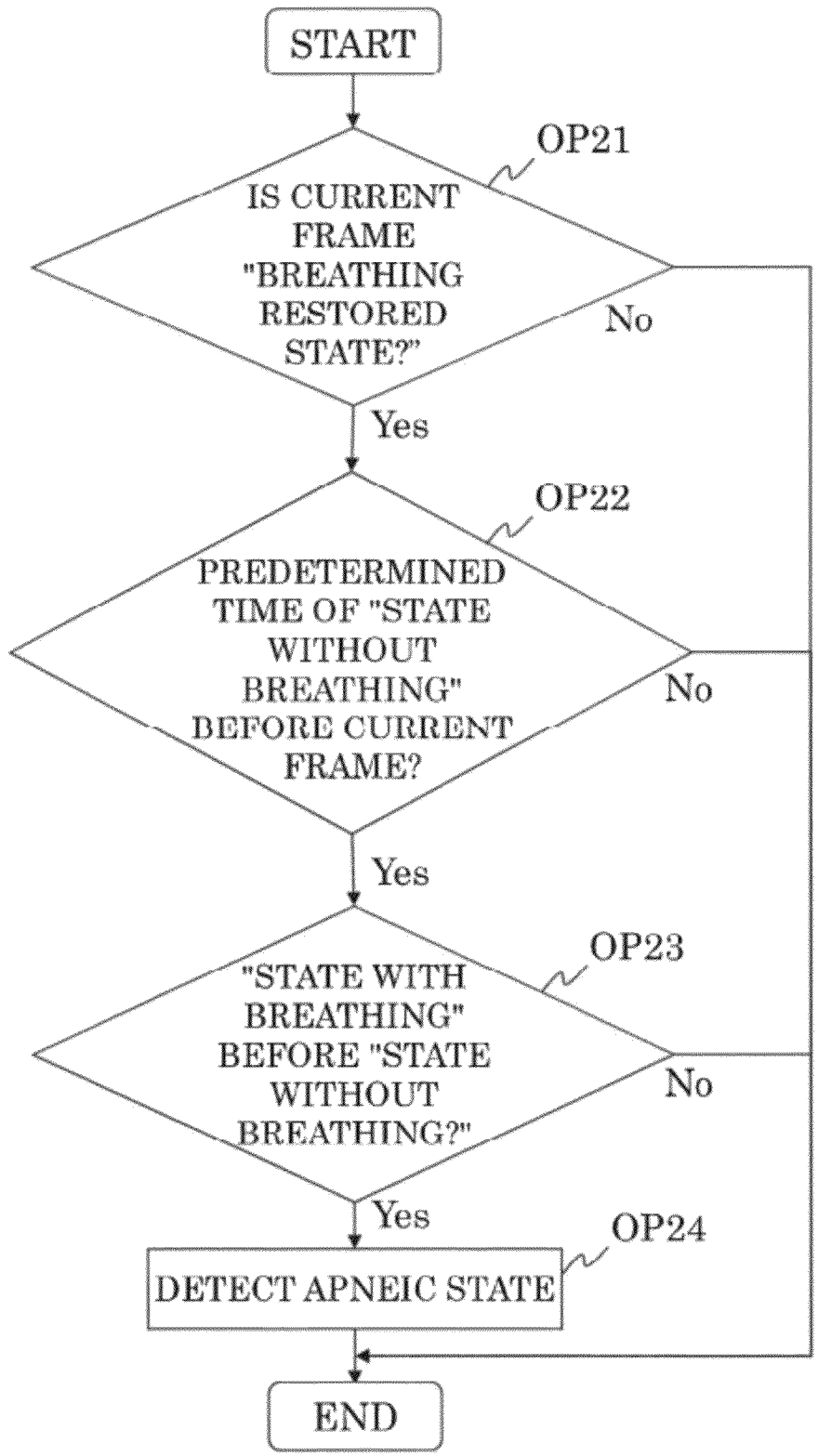
FIG. 12 is a flow of an example of the apneic state detecting processing performed by the state transition examining unit.

FIG. 12 is a diagram depicting a flow of an example of the apneic state detecting processing performed by the state transition examining unit 141 of the apnea determining unit 14. When the sleep state of the current sound frame is input from the sleep state determining unit 13, the state transition examining unit 141 starts the apneic state determination processing.

The state transition examining unit 141 determines whether or not the sleep state of the current sound frame is the "breathing restored state" (OP21).

If the sleep state of the current sound frame is not the "breathing restored state" (OP21: No), that is, if the sleep state of the current sound frame is the "state without breathing" or the "state with breathing," the state transition examining unit 141 ends the apneic state determination processing.

If the sleep state of the current sound frame is the "breathing restored state" (OP21: Yes), the state transition examining unit 141 examines in reverse chronological order the history of the sleep states of the sound frame stored in the state memory 143.

The state transition examining unit 141 examines in reverse chronological order the history of the sleep states of the sound frame and examines whether or not the "state without breathing" continues for a certain duration before the current sound frame (OP22). If the state without breathing continues for ten seconds or longer, the state is determined as an apneic state. However, if a state in which the subject is not breathing continues for a few minutes or longer, a sound pickup microphone may face in a direction opposite to the subject. Therefore, the state transition examining unit 141 examines whether or not the "state without breathing" is continuing for ten seconds or longer and less than two minutes, for example. It should be noted that duration of the "state without breathing" can be detected with the number of continuous sound frames in which the sleep state is the "state without breathing." For example, in the case where one sound frame is two seconds, if the number of continuous sound frames in which the sleep state is the "state without breathing" is five or more, the fact that the "state without breathing" is continuing for ten seconds or longer is detected.

If the "state without breathing" does not continue for a predetermined duration (OP22: No), the subject may just have produced the characteristic sound, so that it may not be determined that the subject is in an apneic state. Therefore, the state transition examining unit 141 ends the apneic state determination processing.

If the "state without breathing" continues for a predetermined duration (OP22: Yes), the state transition examining unit 141 examines whether or not the "state with breathing" exists before the "state without breathing" (OP23). If the "state with breathing" does not exist before the "state without breathing" (OP23: No), since it may not be determined that the subject is in an apneic state, the state transition examining unit 141 ends the apneic state determination processing.

If the "state with breathing" exists before the "state without breathing" (OP23: Yes), the state transition examining unit 141 detects the fact that the subject is in an apneic state (OP24). The state transition examining unit 141 outputs an apneic state detection result to the output unit 15 and ends the apneic state detecting processing.

<<An Operation Example of the Sleep Apnea Syndrome Testing Apparatus>>

Figure 13:
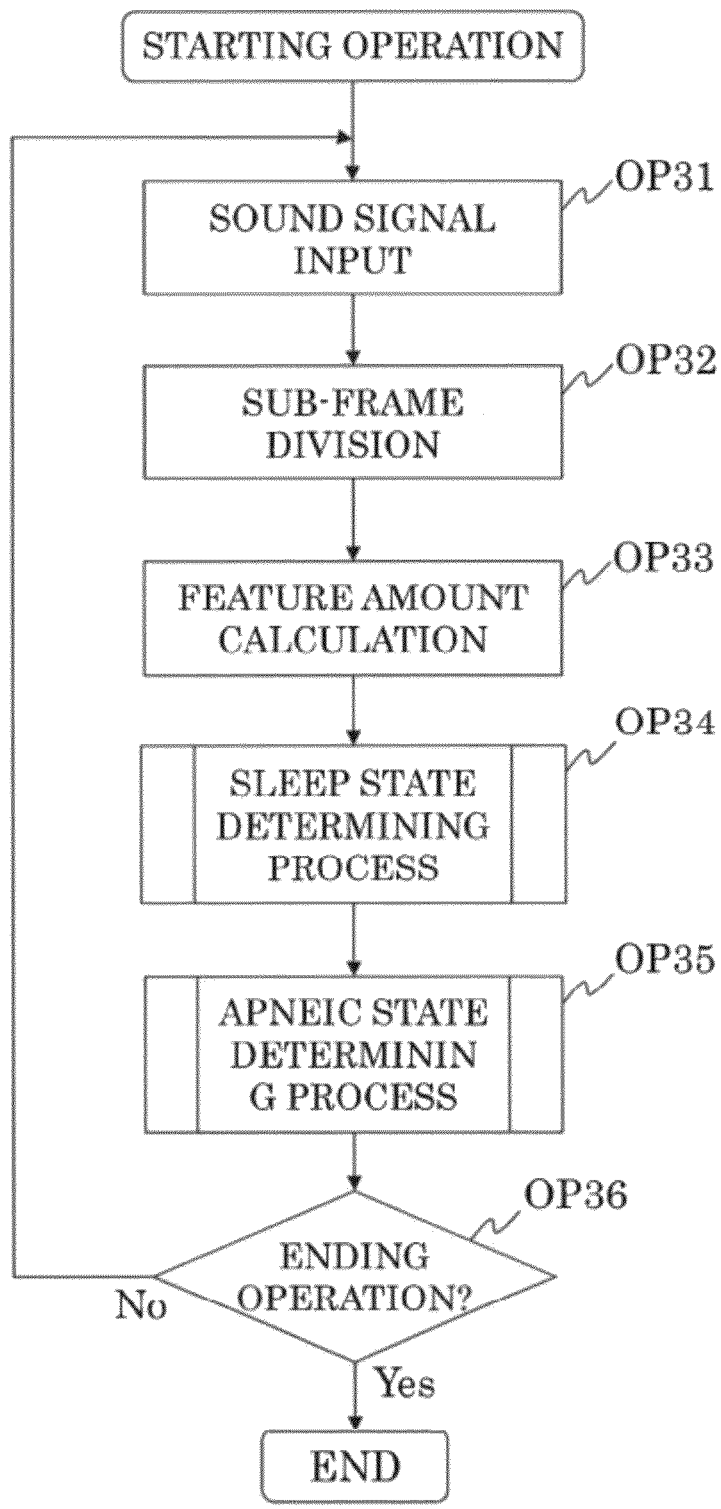
FIG. 13 is a flow of an example of sleep apnea syndrome testing processing performed by the testing apparatus.

FIG. 13 is a diagram depicting a flow of an example of sleep apnea syndrome testing processing performed by the testing apparatus 1.

When the subject 3 (FIG. 2) goes to sleep, the subject 3 turns on the testing apparatus 1, thereby starting a test for sleep apnea syndrome. The subject 3 orients the microphone 2 (FIG. 2) toward a direction in which a breath sound and a voice produced by the subject 3 and a body movement sound of the subject can be accurately collected. For example, the microphone 2 is installed above the sleeping subject 3. Thereafter, the subject 3 goes to sleep.

When the testing apparatus 1 receives from the subject 3 an operation to start a test for sleep apnea syndrome, the testing apparatus 1 starts the sleep apnea syndrome testing processing.

The input unit 11 of the testing apparatus 1 receives an input of a sound signal from the microphone 2 (OP31). The sound signal is converted into a sound frame through the analog-digital converter 17 (FIG. 2) and the buffer 18 (FIG. 2), and then input to the sub-frame dividing unit 121 of the sound analyzing unit 12.

When the sound frame is input, the sub-frame dividing unit 121 divides the sound frame into sub-frames (OP32). The sub-frame dividing unit 121 outputs the sound frame, which is divided into the sub-frames, to the time/frequency converting unit 122.

When the sound frame, which is divided into the sub-frames, is input, the time/frequency converting unit 122 of the sound analyzing unit 12 Fourier transforms the sound signal included in the sound frame into a sound signal in a frequency domain. The time/frequency converting unit 122 outputs the sound frame converted into the sound signal in the frequency domain to the power spectrum calculating unit 123. When the power spectrum calculating unit 123 receives the sound frame converted into the sound signal in the frequency domain, the power spectrum calculating unit 123 calculates a power spectrum as a feature amount for each sub-frame included in the sound frame (OP33). The power spectrum calculating unit 123 outputs power spectrums of all the sub-frames included in the calculated sound frame to the sleep state determining unit 13.

When the power spectrums of all the sub-frames included in the sound frame are input, the sleep state determining unit 13 performs, for example, the sound signal duration calculating processing illustrated in FIG. 7 and the sleep state determining processing illustrated in FIG. 9, thereby determining the sleep state of the sound frame (OP34). The sleep state determining unit 13 outputs the determined sleep state of the sound frame to the apnea determining unit 14.

When the sleep state of the sound frame is input, the apnea determining unit 14, performs, for example, the apneic state detecting processing illustrated in FIG. 12, thereby detecting the apneic state of the subject from the history of the sleep states of the sound frame (OP35). The apnea determining unit 14 outputs a detection result of the apneic state of the subject to the output unit 15 (FIG. 2).

The output unit 15 outputs the detection result of the apneic state to at least one of the network 5, the display 6, the speaker 7, and the secondary storage 8.

The testing apparatus 1 determines whether or not the subject 3 performs an operation to end the test for sleep apnea syndrome (OP36). If the subject 3 does not perform the operation to end the test for sleep apnea syndrome (OP36: No), the processing returns to OP31. That is, while the subject 3 is sleeping, the processes of OP31 through OP35 are repeated.

When the subject 3 wakes up and operates the testing apparatus 1 to perform the operation to end the test for sleep apnea syndrome, the testing apparatus 1 senses the ending operation (OP36: Yes), and the test for sleep apnea syndrome is ended.

Effects of the First Embodiment

The sleep apnea syndrome testing apparatus 1 of the first embodiment detects an apneic state of a subject using a characteristic sound produced when a patient of sleep apnea syndrome transitions from an apneic state to a breathing state. That is, a sound from the subject during sleep is analyzed, and it is determined whether or not the subject is in an apneic state depending upon whether the sound includes a characteristic sound. Therefore, without equipping a subject with a device, a simple test for sleep apnea syndrome can be implemented using sound. Furthermore, because a determination is made using frequency characteristics obtained by analyzing sound, false detection of an apneic state can be prevented from occurring as compared with a determination that is based on only sound volume, resulting in the improved accuracy of detecting an apneic state.

Further, the testing apparatus 1 determines whether or not the sound signal included in the sound frame is a characteristic sound or a breath sound, and determines the sleep state of the sound frame as any one of the "state with breathing," the "state without breathing," and the "breathing restored state." If the sleep state of the sound frame is determined as the "breathing restored state," the testing apparatus 1 examines the history of the sleep states of the sound frame to determine whether or not the sleep state transitions from the "state with breathing," through a predetermined duration of the state "without breathing," to the "breathing restored state" in this order. If the sleep state of the sound frame transitions from the "state with breathing," through a predetermined duration of the "state without breathing," to the "breathing restored state" in this order, the testing apparatus 1 detects the fact that the subject is in an apneic state. Thus, false detection of an apneic state due to false detection of a characteristic sound or the like can be prevented from occurring, resulting in the improved accuracy of detecting an apneic state.

For a subject, a test for sleep apnea syndrome can simply be performed using the testing apparatus 1. The subject can be informed of his/her apneic state during sleep by a test result of sleep apnea syndrome from the testing apparatus 1, and if the subject is suspected of having sleep apnea syndrome, the subject can decide to undergo a close examination in a specialized agency.

According to the sleep apnea syndrome testing apparatus of the disclosure, an apneic state during sleep can be detected.

A Modified Example of the First Embodiment

The sleep state determining unit 13 and the apnea determining unit 14 of the testing apparatus 1 of the first embodiment may be configured as follows. If it is detected that a sound frame includes a characteristic sound, the sleep state determining unit 13 outputs to the apnea determining unit 14 a detection result indicating that the characteristic sound has been detected. If the detection result indicating that the characteristic sound has been detected is input from the sleep state determining unit 13, the apnea determining unit 14 detects the fact that the sleep state of the subject is an apneic state. The apnea determining unit 14 outputs the detection result of the apneic state to the output unit 15 (FIG. 2).

Further, the signal duration calculating unit 131 of the testing apparatus 1 of the first embodiment has determined the continuing interval of the sound signal as described in the examples illustrated in FIG. 7 and FIG. 8. Instead, the signal duration calculating unit 131 may predetermine the number of sub-frames T-t, previous to a reference sub-frame T, correlation coefficients between which are determined. The number w of previous sub-frames with the reference sub-frame T is referred to as the window size. When the signal duration calculating unit 131 determines a correlation coefficient between each of sub-frames included in a window and a reference sub-frame, the signal duration calculating unit 131 shifts the window, and now determines a correlation coefficient with respect to a next reference sub-frame T−1. For example, if a window size w is 2, when the signal duration calculating unit 131 determines a correlation coefficient between a reference sub-frame T and a preceding sub-frame T−1, the signal duration calculating unit 131 shifts the window, and now sets a reference sub-frame to the sub-frame T−1. The signal duration calculating unit 131 determines a correlation coefficient between the reference sub-frame T−1 and a sub-frame T−2 included in the window. Furthermore, the signal duration calculating unit 131 shifts the window, sets a reference to a sub-frame T−2, and determines a correlation coefficient between the sub-frame T−2 and a sub-frame T−3 included in the window. In this manner, the signal duration calculating unit 131 shifts in reverse chronological order the window to gradually shift a reference sub-frame, and determines correlation coefficients. If the correlation coefficient is smaller than the threshold value, a sound signal in a present reference sub-frame T and a sound signal in a sub-frame T-t are deemed to be different sound signals. The signal duration calculating unit 131 determines a boundary between a sub-frame T-t and a sub-frame T-t+1 as a boundary of a continuing interval of the sound signal.

Second Embodiment

Because a sleep apnea syndrome testing apparatus of a second embodiment has a configuration common to the configuration of the testing apparatus 1 of the first embodiment, only different points will be described. In the sleep apnea syndrome testing apparatus of the second embodiment, a sleep state determining unit has a configuration different from that of the sleep state determining unit 13 of the testing apparatus 1 of the first embodiment.

Figure 14:
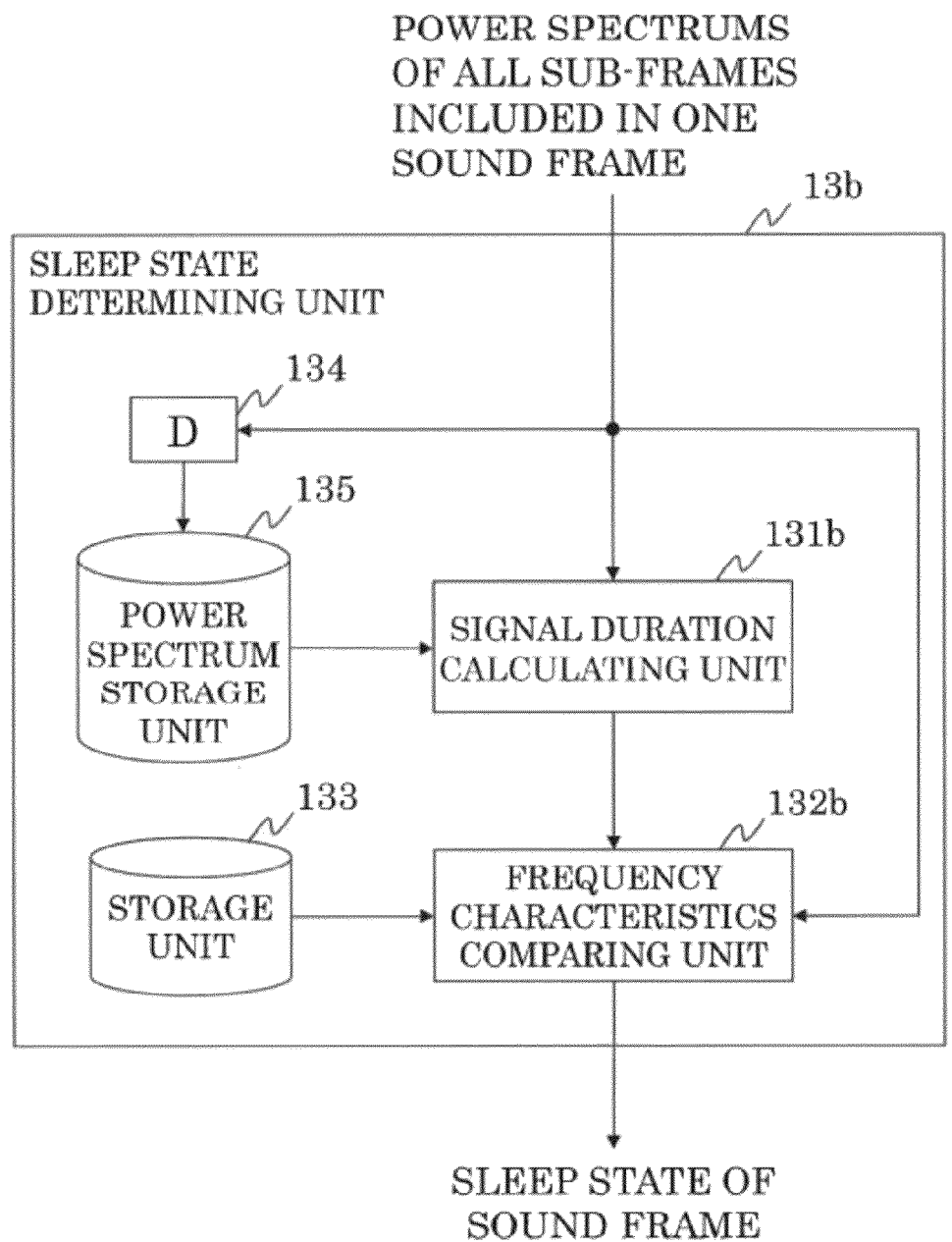
FIG. 14 is a diagram depicting a configuration example of the sleep state determining unit.

FIG. 14 is a diagram depicting a configuration example of the sleep state determining unit 13b of the testing apparatus of the second embodiment. The sleep state determining unit 13b of the second embodiment includes a signal duration calculating unit 131b, a frequency characteristics comparing unit 132b, a storage unit 133, a delay element 134, and a power spectrum storage unit 135.

When the sleep state determining unit 13b receives power spectrums of all sub-frames included in a sound frame, the power spectrums of all the sub-frames included in the sound frame are input in the delay element 134, the signal duration calculating unit 131b, and the frequency characteristics comparing unit 132b. When power spectrums of all sub-frames included in one sound frame are input, the delay element 134 stores the power spectrums of all the sub-frames included in one sound frame into the power spectrum storage unit 135 after a delay of one-frame processing.

The power spectrum storage unit 135 stores therein power spectrums of all sub-frames included in a predetermined time of a sound frame.

The signal duration calculating unit 131b obtains power spectrums of all sub-frames included in one sound frame as input. The signal duration calculating unit 131b calculates, based on the power spectrums of all the sub-frames included in one sound frame, a continuing interval and duration of the sound signal included in the sound frame. Processing for calculating duration of a sound signal included in a sound frame may be the same as the processing described with regard to the signal duration calculating unit 131 of the first embodiment.

The signal duration calculating unit 131b determines a correlation coefficient $r_T(t)$ between a sub-frame T and a sub-frame T-t, previous to the sub-frame T by t, by using the expression 1, for example. At this time, in the signal duration calculating unit 131 of the first embodiment, an initial value of the variable T, indicating a sub-frame number, has been 1. In the signal duration calculating unit 131b of the second embodiment, an initial value of the variable T, indicating a sub-frame number, is 0.

Figure 15:
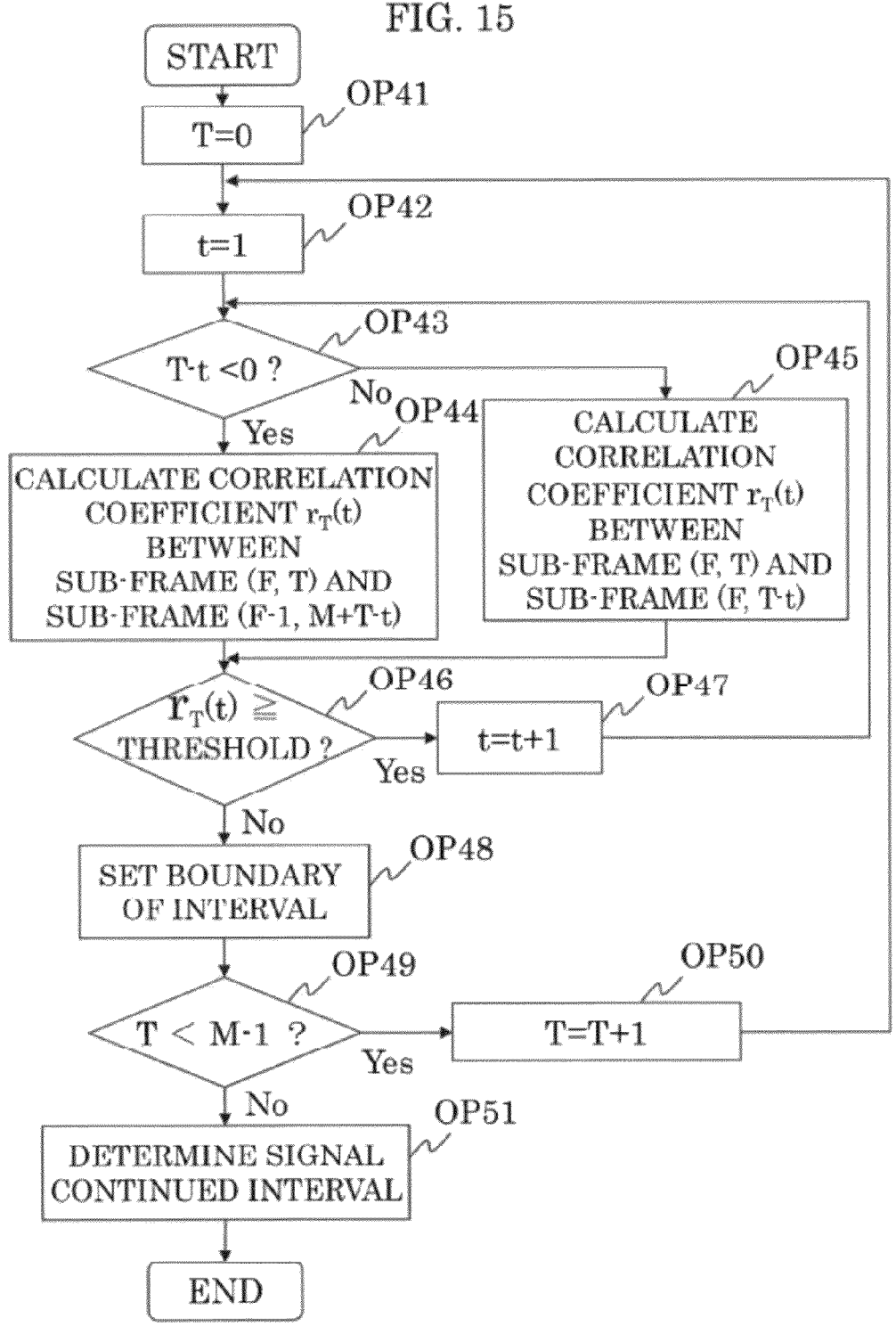
FIG. 15 is an example of a flow of the sound signal duration calculating processing performed by the signal duration calculating unit.

FIG. 15 is a diagram depicting an example of a flow of the sound signal duration calculating processing performed by the signal duration calculating unit 131b. In FIG. 15, a first sub-frame included in a sound frame F being processed (F being a natural number including 0) is expressed as a sub-frame (F, 0). A (T+1)-th sub-frame from the first sub-frame, included in the sound frame F, is expressed as a sub-frame (F, T).

When the signal duration calculating unit 131b receives the power spectrums of all the sub-frames included in the sound frame from the sound analyzing unit 12, the signal duration calculating unit 131b starts the sound signal duration calculating processing.

The signal duration calculating unit 131b sets an initial value of a variable T indicating a sub-frame to 0 (OP41). A range of the variable T, indicating sub-frames, is 0≤T≤M−1 (M being the number of sub-frames included in one frame).

Next, the signal duration calculating unit 131b sets an initial value of a variable t indicating the number of sub-frames previous to the sub-frame T, to 1 (OP42). A range of the variable t is 1≤t.

The signal duration calculating unit 131b determines whether or not T-t is smaller than 0 (OP43).

If T-t is smaller than 0 (OP43: Yes), a sub-frame previous to the sub-frame (F, T) by t represents a sub-frame included in a sound frame F−1 just before the sound frame F. Therefore, if T-t is smaller than 0 (OP43: Yes), the signal duration calculating unit 131b determines a correlation coefficient $r_T(t)$ between the sub-frame (F, T) included in the sound frame F and the sub-frame (F−1, M+T-t) included in the sound frame F−1 (OP44). The signal duration calculating unit 131b reads out from the power spectrum storage unit 135 a power spectrum value of the sub-frame (F−1, M+T-t) included in the sound frame F−1 just before the sound frame F, and determines the correlation coefficient $r_T(t)$ using the expression 1.

If T-t is equal to or greater than 0 (OP43: No), a sub-frame previous to the sub-frame (F, T) by t is included in the sound frame F. Therefore, the signal duration calculating unit 131b determines a correlation coefficient $r_T(t)$ between the sub-frame (F, T) and the sub-frame (F, T-t) previous to the sub-frame (F, T) by t (OP45). The signal duration calculating unit 131b determines the correlation coefficient $r_T(t)$ using the expression 1.

The signal duration calculating unit 131b determines whether or not a calculated value of the correlation coefficient $r_T(t)$ is equal to or greater than a predetermined threshold value (OP46). For example, the predetermined threshold value is 0.7.

If the calculated value of the correlation coefficient $r_T(t)$ is equal to or greater than the threshold value (OP46: Yes), the sound signal included in the sub-frame (F, T) and the sound signal included in the sub-frame (F, T-t) are deemed to be the same sound signal. Alternatively, if the calculated value of the correlation coefficient $r_T(t)$ is equal to or greater than the threshold value (OP46: Yes), the sound signal included in the sub-frame (F, T) and the sound signal included in the sub-frame (F−1, M+T-t) are deemed to be the same sound signal. Therefore, if the calculated value of the correlation coefficient $r_T(t)$ is equal to or greater than the threshold value, then the signal duration calculating unit 131b determines a correlation coefficient $r_T(t)$ between the sub-frame (F, T) and a preceding sub-frame of the sub-frame (F−1, M+T-t). That is, the signal duration calculating unit 131b sets the variable t to t+1 (OP47). Then, the processing returns to OP43, and a correlation coefficient $r_T(t)$ between the sub-frame (F, T) and the sub-frame (F−1, M+T-t) is determined.

If the calculated value of the correlation coefficient $r_T(t)$ is smaller than the threshold value (OP46: No), the sound signal included in the sub-frame (F, T) and the sound signal included in the sub-frame (F, T-t) are deemed to be different sound signals. Alternatively, if the calculated value of the correlation coefficient $r_T(t)$ is smaller than the threshold value (OP46: No), the sound signal included in the sub-frame (F, T) and the sound signal included in the sub-frame (F−1, M+T-t) are deemed to be different sound signals. If the calculated value of the correlation coefficient $r_T(t)$ is smaller than the threshold value (OP46: No), the signal duration calculating unit 131b ends the processing for determining the correlation coefficient $r_T(t)$ between the sub-frame (F, T) and the sub-frame previous to the sub-frame (F, T) by t.

If the calculated value of the correlation coefficient $r_T(t)$ is smaller than the threshold value (OP46: No), the signal duration calculating unit 131b determines a boundary between the sub-frame (F, T-t) and a following sub-frame as a boundary of a continuing interval of the sound signal (OP48). Alternatively, the signal duration calculating unit 131b determines a boundary between the sub-frame (F−1, M+T-t) and a following sub-frame as a boundary of a continuing interval of the sound signal (OP48).

Next, the signal duration calculating unit 131b determines whether or not the variable T is smaller than M−1 (OP49). That is, the signal duration calculating unit 131b determines whether or not the processing for determining the correlation coefficients $r_T(t)$ between all the sub-frames (F, T) included in the sound frame F and the sub-frames previous to the sub-frames (F, T) by t has been ended.

If the variable T is smaller than M−1 (OP49: Yes), it is indicated that the processing for determining the correlation coefficients $r_T(t)$ between all the sub-frames (F, T) included in the sound frame F and the sub-frames previous to the sub-frames (F, T) by t has not been ended. In order to determine correlation coefficients $r_T(t)$ between sub-frames (F, T+1) next to the sub-frames (F, T) and sub-frames previous to the sub-frames (F, T+1) by t, the signal duration calculating unit 131b sets the variable T to T+1 (OP50). Then, the processing returns to OP42.

If the variable T is equal to or greater than M−1 (OP49: No), it is indicated that the processing for determining the correlation coefficients $r_T(t)$ between all the sub-frames (F, T) included in the sound frame F and the sub-frames previous to the sub-frames (F, T) by t has been ended. The signal duration calculating unit 131b determines, based on the boundaries of the intervals determined in OP48, intervals in which sound signals continue, and calculates duration of the sound signal included in each interval (OP51). The signal duration calculating unit 131b counts the number of the sub-frames included in each interval and calculates duration of the sound signal in each interval.

In the example illustrated in FIG. 15, the signal duration calculating unit 131b performs processing for determining correlation coefficients $r_T(t)$ between sub-frames (F, T) and sub-frames previous to the sub-frames (F, T) by t until a value of the correlation coefficients $r_T(t)$ with the sub-frames (F, T) becomes smaller than a threshold value. That is, if a sound signal included in the sub-frame (F, T) extends over the sound frame F−1 just before the sound frame F, the signal duration calculating unit 131b calculates duration of the sound signal continuing from the preceding sound frame F−1 to the sound frame F.

The signal duration calculating unit 131b outputs, to the frequency characteristics comparing unit 132b, an interval and duration of the sound signal extending to the sound frame F−1, an interval and duration of the other sound signal included in the sound frame F, and power spectrums of sub-frames of the sound frame F−1 including a sound signal part extending to the sound frame F−1.

The frequency characteristics comparing unit 132b obtains power spectrums of all the sub-frames included in the sound frame F and the interval and the duration of the sound signal included in the sound frame F as input. Further, if the sound signal included in the sound frame F extends to the sound frame F−1 just before the sound frame F, the frequency characteristics comparing unit 132b also obtains power spectrums of the sub-frames including the sound signal part extending to the preceding sound frame F−1 as input. In the same manner as the frequency characteristics comparing unit 132 of the first embodiment, the frequency characteristics comparing unit 132b extracts an interval in which duration of the sound signal is equal to or greater than a predetermined value. The frequency characteristics comparing unit 132b calculates the number of formants and variance of a fine structure power spectrum from the power spectrums of the sub-frames including the sound signal in the extracted interval. If the sound signal included in the sound frame F extends to the preceding sound frame F−1, the frequency characteristics comparing unit 132b calculates the number of formants and variance of a fine structure power spectrum of the sound signal in the interval including the sub-frames of the sound frame F−1 to which the sound signal extends.

The frequency characteristics comparing unit 132b compares the number of formants and the value of the variance of the fine structure power spectrum of the sound signal included in the extracted interval, with a range of comparison values of the number of formants and the variance of the fine structure power spectrum of the characteristic sounds A to C and the breath sound, stored in the storage unit 133. As a result of the comparison, the frequency characteristics comparing unit 132b determines the sleep state of the sound frame F as any one of the "state with breathing," the "state without breathing," and the "breathing restored state." That is, the frequency characteristics comparing unit 132b performs the sleep state determining processing illustrated in FIG. 9.

The frequency characteristics comparing unit 132b outputs the sleep state of the current sound frame to the apnea determining unit 14.

Effects of the Second Embodiment

The sleep state determining unit 13b includes a power spectrum storage unit 135 in which values of power spectrums of all the sub-frames included in the past sound frames are stored. Thus, the signal duration calculating unit 131b can calculate duration of the sound signal using the power spectrums of the sub-frames included in a sound frame just before a current sound frame. By using the power spectrums of the sub-frames included in the preceding sound frame, for example, even if a sound signal extends to the preceding sound frame, the sleep state of the sound frame can be determined with high accuracy.

Figure 16:
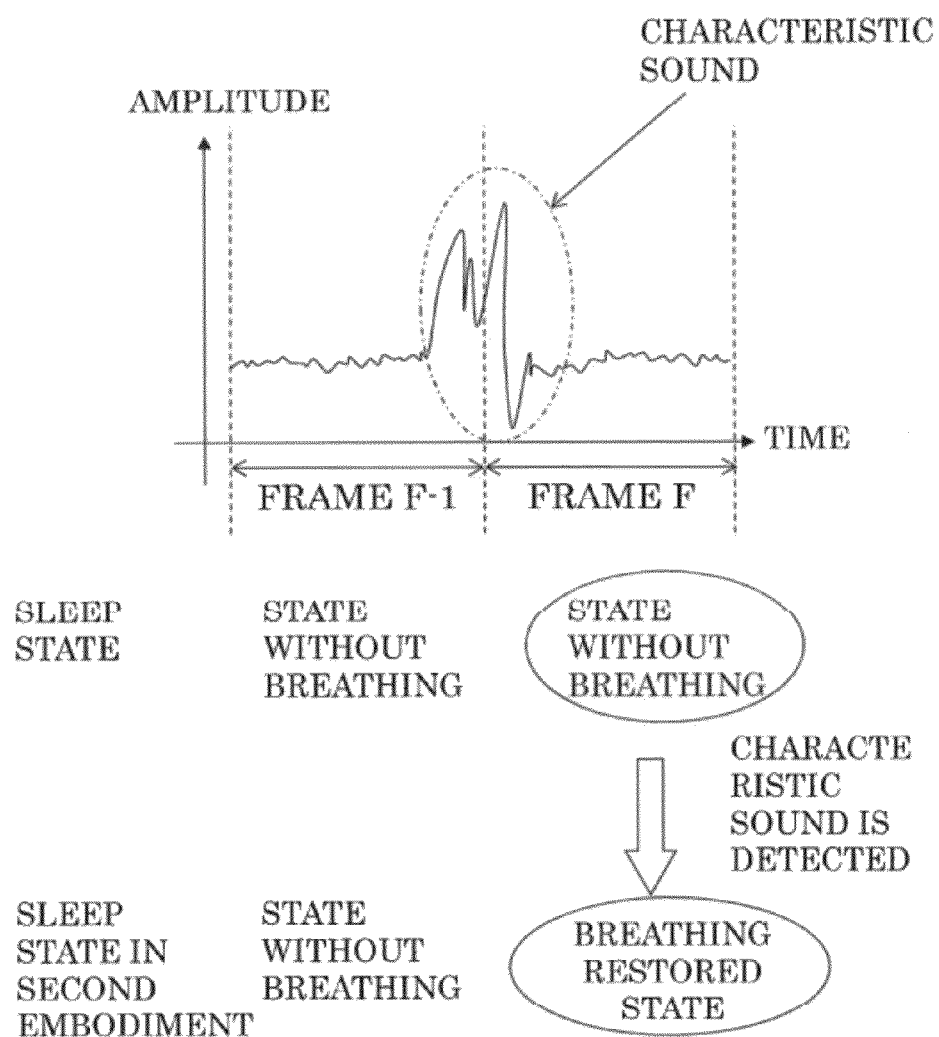
FIG. 16 is a diagram of an example of a case in which a sound signal included in the sub-frame (F, T) extends over the sound frame F−1 just before the sound frame F.

FIG. 16 is a diagram of an example for illustrating effects of the second embodiment. In the example illustrated in FIG. 16, a sound signal of a characteristic sound is divided into a sound frame F−1 and a sound frame F, adjacent to each other. The sleep state determining unit 13 of the first embodiment may not calculate duration of the sound signal using power spectrums of sub-frames included in the preceding sound frame F−1. That is, the sleep state determining unit 13 of the first embodiment calculates duration, the number of formants, and variance of a fine structure power spectrum of only a sound signal included in the sound frame F. Therefore, in the example illustrated in FIG. 16, duration of the sound signal of the characteristic sound included in each of the sound frame F−1 and the sound frame F might be less than a predetermined value. Further, values of sleep state determination parameters (the number of formants and variance of a fine structure power spectrum) of the sound signal of the characteristic sound included in each of the sound frame F−1 and the sound frame F may not be included in a range of comparison values of the number of formants and variance of a fine structure power spectrum of any one of the characteristic sounds A to C and the breath sound. That is, in the example illustrated in FIG. 16, the sleep state determining unit 13 of the first embodiment may determine the sleep states of sound frame F−1 and the sound frame F as the "state without breathing," leading to an error in the sleep state.

Further, a sound signal of a breath sound may extend over the sound frame F−1 and the sound frame F. Values of sleep state determination parameters of the sound signal of the breath sound included in the sound frame F−1 or the sound frame F may be included in a range of values that may be taken by the sleep state determination parameters of any one of the characteristic sounds A to C. Therefore, although the breath sound is included in the sound frame F−1 and the sound frame F, the sleep state determining unit 13 of the first embodiment may determine the sleep state of the sound frame F−1 or the sound frame F as the "breathing restored state," leading to an error in the sleep state.

The sleep state determining unit 13b of the second embodiment can calculate duration of the sound signal included in the sound frame F using power spectrums of sub-frames included in the preceding sound frame F−1. Further, if the sound signal extends to the preceding sound frame F−1, power spectrums of sub-frames of the sound signal extending to the preceding sound frame F−1 can be used to perform the sleep state determining processing of the sound frame F. Therefore, the sleep state determining unit 13b of the second embodiment can detect the fact that the sound frame F in FIG. 16 includes a characteristic sound and determine the sleep state of the sound frame F as the "breathing restored state." That is, the sleep state determining unit 13b of the second embodiment can reduce errors in the determination of the sleep state of the sound frame.

A Modified Example of the Second Embodiment

When duration of the sound signal continuing across two or more sound frames is calculated, instead of the processing in OP44 in FIG. 15, the signal duration calculating unit 131b may perform the following processing.

In OP43 of FIG. 15, if T-t is smaller than 0, the signal duration calculating unit 131b calculates a correlation coefficient $r_T(t)$ between the sub-frame (F, T) and the sub-frame (F-n, Mn+T-t) previous to the sub-frame (F, T) by t. That is, the sub-frame previous to the sub-frame (F, T) by t is included in the sound frame F-n. Here, n is the largest natural number satisfying the following expression 3, not including 0.

$$|T-t| > (n-1) \times M \qquad \text{Expression 3}$$

Thus, even if a sound signal continues from a sub-frame included in the sound frame F-n to a sub-frame (F, T) included in the sound frame F, duration of the sound signal can be calculated. That is, even if a sound signal continues across two or more sound frames, duration of the sound signal can be calculated.

Third Embodiment

Because a sleep apnea syndrome testing apparatus of a third embodiment has a configuration common to the configuration of the testing apparatus 1 of the first embodiment, only different points will be described.

Figure 17:
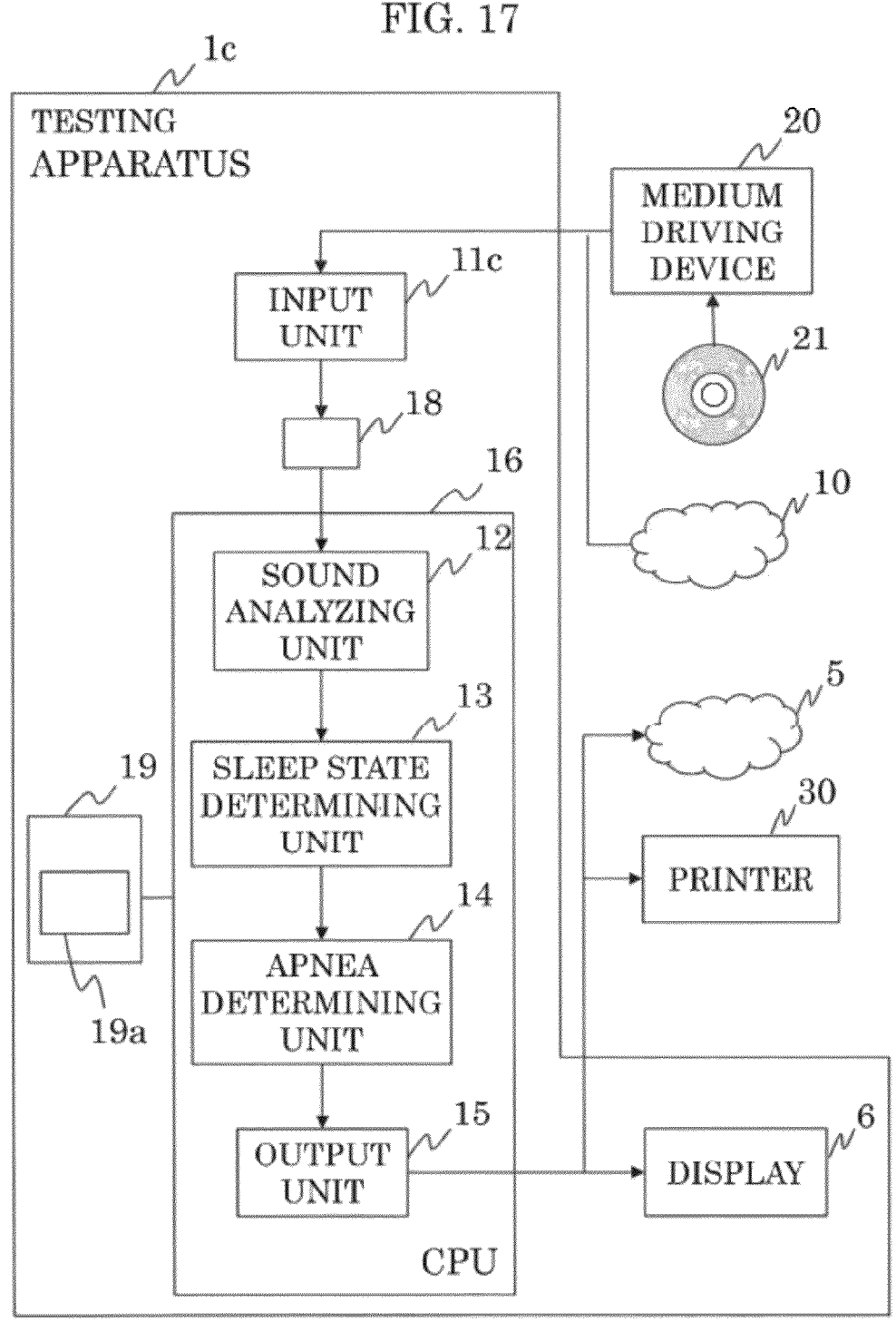
FIG. 17 is a diagram depicting a configuration example of a sleep apnea syndrome testing system.

FIG. 17 is a diagram depicting a configuration example of a sleep apnea syndrome testing system. The sleep apnea syndrome testing system of the third embodiment includes a testing apparatus 1c and a medium driving device 20 connected with the testing apparatus 1c. The testing apparatus 1c of the third embodiment carries out a test for sleep apnea syndrome from sound data of a subject during sleep, recorded in advance.

The testing apparatus 1c includes an input unit 11c, a CPU 16, main memory 19, an output unit 15, a buffer 18, and a display 6.

The input unit 11c is connected with a medium driving device 20 that reads out sound data from a portable recording medium 21, and sound data stored in the portable recording medium 21 is input by the medium driving device 20. Alternatively, the input unit 11c is connected with a network 10, and sound data is input from a terminal of a subject via the network 10. At this time, the input sound data has already been converted into a digital signal. The input unit 11c outputs sound data to the buffer 18.

The buffer 18, the main memory 19, and the CPU 16 are the same as the components described in the first embodiment, so that descriptions thereof are omitted. The CPU 16 reads out a sleep apnea syndrome testing program held in the main memory 19 and acts as the sound analyzing unit 12, the sleep state determining unit 13, and the apnea determining unit 14. The sound analyzing unit 12, the sleep state determining unit 13, and the apnea determining unit 14 are also the same as the components described in the first embodiment, so that descriptions thereof are omitted.

The output unit 15 obtains a detection result of an apneic state from the apnea determining unit 14 as input. The output unit 15 outputs the detection result of the apneic state to the network 5, a printer 30, and the display 6. The detection result of the apneic state output from the output unit 15 may be displayed on the display 6. The detection result of the apneic state output from the output unit 15 may be transmitted via the network 5 to the subject terminal. The detection result of the apneic state output from the output unit 15 may be output to the printer 30 and printed out on a print medium.

<A Hardware Configuration of the Sleep Apnea Syndrome Testing Apparatuses>

As the testing apparatus 1 of the first embodiment, the testing apparatus of the second embodiment, and the testing apparatus 1c of the third embodiment (hereinafter, collectively referred to as the "testing apparatus"), information processing apparatuses (computers) may be adopted. The information processing apparatuses may be general purpose computers such as personal computers or dedicated purpose computers that carry out a test for sleep apnea syndrome. Further, the testing apparatuses of the first embodiment and the second embodiment may be portable telephones.

The testing apparatus includes a processor, main memory, an inputting device, an outputting device, secondary storage, and an interface device to peripheral devices, such as a communications interface device. The main memory and the secondary storage are computer readable recording media.

The testing apparatus can implement a function serving a predetermined purpose by the processor loading a program stored in a recording medium into a working space of the main memory and executing the program, and the peripheral devices being controlled through the execution of the program.

The processor is, for example, a CPU (Central Processing Unit) and a DSP (Digital Signal Processor). The main memory includes, for example, a ROM (Read Only Memory) and a RAM (Random Access Memory).

The secondary storage is, for example, EPROM (Erasable Programmable ROM) or a hard disk drive (Hard Disk Drive). Further, the secondary storage can include a removable medium, i.e., a portable recording medium. The removable medium is, for example, USB (Universal Serial Bus) memory or a disk recording medium such as a CD (Compact Disc) and a DVD (Digital Versatile Disc).

The communications interface device is connected with a wired network and a wireless network. The communications interface device is, for example, a LAN (Local Area Network) interface board and a wireless communications circuit for wireless communications.

Furthermore, the peripheral devices include inputting devices such as a keyboard and a pointing device and outputting devices such as a display device and a printer. In addition, the inputting devices may include a voice inputting device such as a microphone. Furthermore, the outputting devices may include a voice outputting device such as a speaker.

A computer used as a testing apparatus accomplishes functions of the sound analyzing unit 12, the sleep state determining unit 13, and the apnea determining unit 14 by a processor executing a sleep apnea syndrome testing program on a recording medium and peripheral devices being controlled. The storage unit 133, the state memory 143, and the power spectrum storage unit 135 are created statically or during the execution of the program, in a storage area of the main memory or the secondary storage.

Fourth Embodiment

Figure 18:
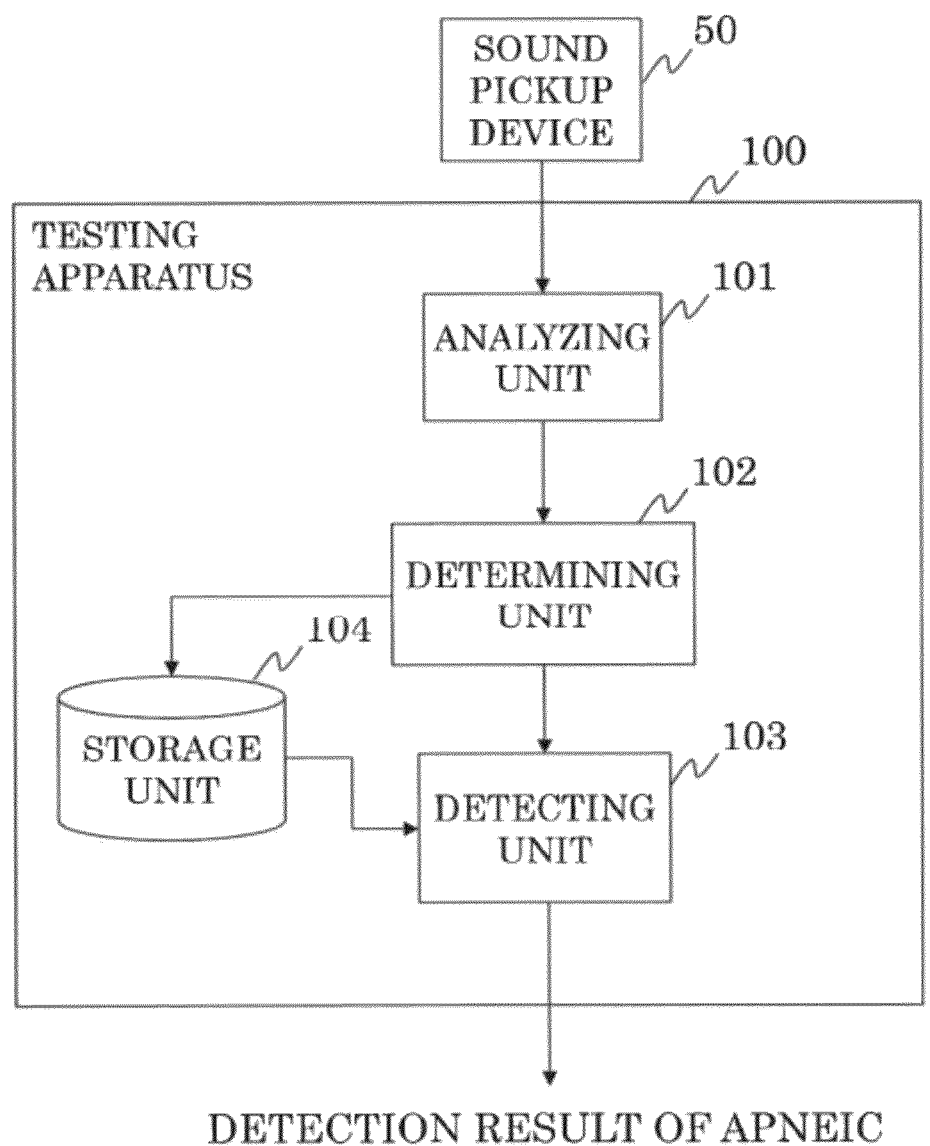
FIG. 18 is a diagram depicting a configuration example of a sleep apnea syndrome testing system.

FIG. 18 is a diagram depicting a configuration example of a sleep apnea syndrome testing system of a fourth embodiment. The sleep apnea syndrome testing system of the fourth embodiment includes a testing apparatus 100 and a sound pickup device 50. The testing apparatus 100 includes an analyzing unit 101, a determining unit 102, a detecting unit 103, and a storage unit 104.

The sound pickup device 50 collects a sound signal resulting from a subject during sleep and outputs the signal to the testing apparatus 100.

The analyzing unit 101 of the testing apparatus 100 obtains the sound signal resulting from the subject during sleep and collected by the sound pickup device as input. The analyzing unit 101 analyzes the input sound signal. The analyzing unit 101 outputs an analysis result of the sound signals to the determining unit 102.

The determining unit 102 obtains the analysis result of the sound signal from the analyzing unit 101 as input. The determining unit 102 determines whether or not the sound signal includes a characteristic sound on the basis of the analysis result by the analyzing unit 101. The characteristic sound is a sound produced when a sleep state recovers from an apneic state to a breathing state. The determining unit 102 outputs a determination result of whether or not the sound signal includes the characteristic sound to the detecting unit 103.

The detecting unit 103 obtains the determination result of whether or not the sound signal includes the characteristic sound as input. The detecting unit 103 detects the apneic state if it is determined that the sound signal includes the characteristic sound. The detecting unit 103 outputs the detection result of the apneic state.

The sleep apnea syndrome testing apparatus 100 determines that the sound signal resulting from the subject during sleep includes a characteristic sound produced when a sleep state recovers from an apneic state into a breathing state. Thus, since an apneic state is not detected unless the characteristic sound is detected, an apneic state during sleep can be detected with high accuracy.

Also, the testing apparatus 100 may be configured as follows. The analyzing unit 101 analyzes an input sound signal every unit time. The analyzing unit 101 outputs an analysis result of the unit time of the sound signal to the determining unit 102.

The determining unit 102 determines whether the unit time of the sound signal includes a characteristic sound. If the unit time of the sound signal does not include a characteristic sound, the determining unit 102 determines whether or not the unit time of the sound signal includes a breath sound.

If the unit time of the sound signal includes a characteristic sound, the determining unit 102 determines that the sleep state is the "breathing restored state."

If the unit time of the sound signal does not include a characteristic sound but includes a breath sound, the determining unit 102 determines that the sleep state is the "state with breathing."

If the unit time of the sound signal does not include either of a characteristic sound and a breath sound, the determining unit 102 determines that the sleep state is the "state without breathing."

The determining unit 102 outputs the determined sleep state to the detecting unit 103 and the storage unit 104.

The storage unit 104 obtains the sleep state from the determining unit 102 as input. The storage unit 104 stores therein sleep states in chronological order. That is, the storage unit 104 holds a history of the sleep states.

The detecting unit 103 obtains the sleep state from the determining unit 102 as input. If the history of the sleep states stored in the storage unit indicates at least a transition from the "state without breathing" to the "breathing restored state," the detecting unit 103 detects an apneic state. The detecting unit 103 outputs a detection result of the apneic state.

The sleep apnea syndrome testing apparatus 100 analyzes a sound signal every unit time and determines whether the unit time of the sound signal includes a characteristic sound and a breath sound. The testing apparatus 100 determines, based on a determination result, that the sleep state of the subject viewed from the unit time of the sound signal is any one of the "breathing restored state," the "state with breathing," and the "state without breathing." If the history of the sleep states of the subject in the unit time indicates at least a transition from the "state without breathing" to the "breathing restored state," the testing apparatus 100 detects the apneic state of the subject. Thus, an apneic state can be detected more carefully, so that the accuracy of detecting an apneic state can be improved.

Also, the analyzing unit 101 of the testing apparatus 100 may calculate duration and frequency characteristics of a sound signal being a sound produced by the subject and being included in the sound signal, and the determining unit 102 may determine whether or not the duration and the frequency characteristics of the sound signal of the sound produced by the subject match a characteristic sound.

Also, the analyzing unit 101 of the testing apparatus 100 may divide a sound signal in a unit time into M time intervals (M: a natural number, not including 0) by a predetermined time interval length, and calculate a power spectrum in each time interval. The determining unit 102 determines a correlation coefficient between a power spectrum of a sound signal in a predetermined time interval T ($0 \leq T \leq M-1$) and a power spectrum of a sound signal in a time interval (T-t) ($0<t$), previous to the time interval T. If the correlation coefficient is equal to or greater than a threshold value, the determining unit 102 may detect a sound signal continuing from the time interval (T-t) to the time interval T to calculate the duration of the sound signal. Furthermore, if the time interval (T-t) is a time interval included in a unit time previous to the present unit time, the determining unit 102 may determine a correlation coefficient between the power spectrum of the sound signal in the time interval T and a power spectrum of the time interval (T-t) included in the unit time previous to the present unit time. Thus, if the correlation coefficient is equal to or greater than a threshold value, a sound signal continuing from the time interval (T-t) included in a unit time previous to the present unit time to the time interval T can be detected. If sound signal continuing from the time interval (T-t) included in a unit time previous to the present unit time to the time interval T is detected, the determining unit 102 can determine that a sound signal in a predetermined unit time includes a characteristic sound or a breath sound with high accuracy. If it is determined that a sound signal in a predetermined unit time includes a characteristic sound or a breath sound with high accuracy, the determining unit 102 can determine a sleep state in a predetermined unit time with high accuracy. As a result, the accuracy of detecting an apneic state during sleep is improved.

The determining unit 102 may calculate sound parameters representing sound characteristics of the sound signal including duration of the sound signal continuing from a time interval (T-t) to a time interval T, the number of formants, and variance properties of a power spectrum. The determining unit 102 may compare the sound parameters with the sound characteristics of the predetermined characteristic sounds and the breath sound to determine that the sleep state is any one of the "breathing restored state," the "state with breathing," and the "state without breathing."

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment(s) of the present inventions have been described in detail, it should be understood that the various changes, substitutions, and alterations could be made hereto without departing from the spirit and scope of the invention.

What is claimed is:

1. A sleep apnea syndrome testing apparatus comprising:
an analyzing unit configured to analyze a sound signal resulting from a subject during sleep and collected by a sound pickup device; and to calculate frequency characteristics of a partial sound signal being a sound produced by the subject and being included in the sound signal; and
a determining unit configured to:
calculate, based on the calculated frequency characteristics, duration of the partial sound signal;
determine whether or not the duration and the frequency characteristics of the partial sound signal match a characteristic sound; and
determine whether or not the sound signal includes a characteristic sound produced when a sleep state of the subject recovers from an apneic state into a breathing state,
wherein the analyzing unit is configured to divide the sound signal in a unit of time into M time intervals by a predetermined time interval length, wherein M is a natural number not including zero, and calculate a power spectrum in each time interval, and
wherein the determining unit is configured to calculate the duration of the partial sound signal by:
calculating a correlation coefficient between a power spectrum of a sound signal in a time interval T, wherein T is greater than or equal to zero and less than or equal to M−1, and a power spectrum of a sound signal in a time interval (T-t), wherein t is a positive integer;
comparing the correlation coefficient with a threshold value;
when the correlation coefficient is greater than the threshold value, detecting a sound signal continuing from the time interval (T-t) to the time interval T; increasing a value of the t by one; and repeating the calculation of the correlation coefficient,
wherein, when the t is equal to or greater than two, the determining unit performs the calculation of the correlation coefficient regarding the time the time interval T and the time interval (T-t) which are not adjacent;
repeating the calculation of the correlation coefficient until the correlation coefficient is smaller than the threshold value; and
calculating duration of the sound signal based on the detection of the sound signal continuing from time interval (T-t) to the time interval T.

2. The sleep apnea syndrome testing apparatus according to claim 1, further comprising a detecting unit configured to detect an apneic state when the sound signal includes the characteristic sound.

3. The sleep apnea syndrome testing apparatus according to claim 2, wherein the analyzing unit is further configured to analyze the sound signal every unit of time;
the determining unit is further configured to:
determine, based on an analysis result by the analyzing unit, whether or not the unit of time of the sound signal includes at least the characteristic sound;
when the unit of time of the sound signal includes the characteristic sound, determine that a sleep state is a "breathing restored state;" and
when the unit of time of the sound signal does not include the characteristic sound or a breath sound, determine that the sleep state is a "state without breathing;" and
the detecting unit is configured to detect an apneic state when the sleep state transitions at least from the "state without breathing" to the "breathing restored state".

4. The sleep apnea syndrome testing apparatus according to claim 3, further comprising a storage unit configured to hold a history of sleep states.

5. The sleep apnea syndrome testing apparatus according to claim 4, wherein the determining unit is further configured to determine that the sleep state is a "state with breathing" when the unit of time of the sound signal does not include the characteristic sound but includes a breath sound, and
wherein the detecting unit is further configured to detect the apneic state when the history of the sleep state stored in the storage unit transitions from "state with breathing," through the "state without breathing," to the "breathing restored state," in this order.

6. The sleep apnea syndrome testing apparatus according to claim 1, wherein the determining unit is further configured to:
calculate sound parameters representing sound characteristics of the sound signal; and determine that the sleep state is any one of a "breathing restored state," a "state with breathing," and a "state without breathing" by comparing the sound parameters with sound characteristics of the characteristic sound and a breath sound.

7. The sleep apnea syndrome testing apparatus according to claim 6, wherein the sound parameters include duration, a number of formants and variance properties of a power spectrum of the sound signal.

8. A test method for sleep apnea syndrome executed by a processor, comprising:
   analyzing, using the processor, a sound signal produced during sleep and collected by a sound pickup device;
   calculating, using the processor and based on a result of the analyzing, duration and frequency characteristics of a partial sound signal being a sound produced by the subject and being included in the sound signal;
   determining, using the processor, whether or not the duration and the frequency characteristics of the partial sound signal match a characteristic sound; and
   determining, using the processor, whether or not the sound signal includes a characteristic sound produced when a sleep state recovers from an apneic state into a breathing state,
   wherein the analyzing comprises dividing the sound signal in a unit of time into M time intervals by a predetermined time interval length, wherein M is a natural number not including zero; and calculating a power spectrum in each time interval, and
   wherein calculating the duration of the partial sound signal comprises:
      calculating a correlation coefficient between a power spectrum of a sound signal in a time interval T, wherein T is greater than or equal to zero and less than or equal to M−1, and a power spectrum of a sound signal in a time interval (T-t), wherein t is a positive integer;
      comparing the correlation coefficient with a threshold value;
      when the correlation coefficient is greater than the threshold value, detecting a sound signal continuing from the time interval (T-t) to the time interval T; increasing a value of the t by one; and repeating the calculation of the correlation coefficient,
      wherein, when the t is equal to or greater than two, the determining unit performs the calculation of the correlation coefficient regarding the time the time interval T and the time interval (T-t) which are not adjacent;
      repeating the calculation of the correlation coefficient until the correlation coefficient is smaller than the threshold value; and
      calculating duration of the sound signal based on the detection of the sound signal continuing from time interval (T-t) to the time interval T.

9. A computer-readable, non-transitory recording medium recording a program for causing a computer operating as a sleep apnea syndrome testing apparatus to execute:
   analyzing a sound signal produced during sleep and collected by a sound pickup device;
   calculating, based on a result of the analyzing, duration and frequency characteristics of a partial sound signal being a sound produced by the subject and being included in the sound signal;
   determining whether or not the duration and the frequency characteristics of the partial sound signal match a characteristic sound; and
   determining whether or not the sound signal includes a characteristic sound produced when a sleep state recovers from an apneic state into a breathing state,
   wherein the analyzing comprises dividing the sound signal in a unit of time into M time intervals by a predetermined time interval length, wherein M is a natural number not including zero; and calculating a power spectrum in each time interval, and
   wherein calculating the duration of the partial sound signal comprises:
      calculating a correlation coefficient between a power spectrum of a sound signal in a time interval T, wherein T is greater than or equal to zero and less than or equal to M−1, and a power spectrum of a sound signal in a time interval (T-t), wherein t is a positive integer;
      comparing the correlation coefficient with a threshold value;
      when the correlation coefficient is greater than the threshold value, detecting a sound signal continuing from the time interval (T-t) to the time interval T; increasing a value of the t by one; and repeating the calculation of the correlation coefficient,
      wherein, when the t is equal to or greater than two, the determining unit performs the calculation of the correlation coefficient regarding the time the time interval T and the time interval (T-t) which are not adjacent;
      repeating the calculation of the correlation coefficient until the correlation coefficient is smaller than the threshold value; and
   calculating duration of the sound signal based on the detection of the sound signal continuing from time interval (T-t) to the time interval T.

* * * * *